(12) United States Patent
Donde et al.

(10) Patent No.: US 8,278,347 B2
(45) Date of Patent: Oct. 2, 2012

(54) THERAPEUTIC COMPOUNDS

(75) Inventors: Yariv Donde, Dana Point, CA (US); Jeremiah H. Nguyen, La Puente, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/176,427

(22) Filed: Jul. 5, 2011

(65) Prior Publication Data

US 2011/0263692 A1   Oct. 27, 2011

Related U.S. Application Data

(63) Continuation of application No. 12/190,165, filed on Aug. 12, 2008, now abandoned, which is a continuation-in-part of application No. 11/742,987, filed on May 1, 2007, now Pat. No. 7,439,372.

(60) Provisional application No. 60/746,275, filed on May 3, 2006, provisional application No. 60/746,386, filed on May 4, 2006.

(51) Int. Cl.
*A61K 31/38* (2006.01)
*A61K 31/19* (2006.01)

(52) U.S. Cl. .......................... 514/448; 514/568; 514/570

(58) Field of Classification Search .................. 514/448, 514/568, 570
See application file for complete search history.

(56) References Cited

U.S. PATENT DOCUMENTS

| | | | |
|---|---|---|---|
| 4,166,452 | A | 9/1979 | Generales |
| 4,256,108 | A | 3/1981 | Theeuwes |
| 4,265,874 | A | 5/1981 | Bonsen |
| 6,437,146 | B1 | 8/2002 | Hattori |
| 6,710,072 | B2 | 3/2004 | Burk |

FOREIGN PATENT DOCUMENTS

| | | |
|---|---|---|
| EP | 0795331 | 9/1997 |
| WO | WO95/17393 | 6/1995 |
| WO | WO95/19964 | 7/1995 |
| WO | WO02/24629 | 3/2002 |
| WO | WO2007/131012 | 11/2007 |

OTHER PUBLICATIONS

U.S. Appl. No. 60/744,236, filed Apr. 4, 2006, Donde.
U.S. Appl. No. 11/009,298, filed Dec. 10, 2004, Donde.
U.S. Appl. No. 60/742,779, filed Dec. 6, 2005, Donde.
U.S. Appl. No. 11/553,143, filed Oct. 26, 2006, Donde.
Dragoli, et al., "Parallel Synthesis of Prostaglandin $E_1$ Analogues," J. Comb. Chem., 1999, 1, pp. 534-539 (XP0002323674).
Stella, Valentino J, Expert Opinion of Therapeutic Patents, Prodrugs as therapeutics, 2004 14(3): 277-280.
Wolff et al. (Burger's Medicinal Chemistry, 5th Ed., vol. 1, pp. 975-977, 1994.
Testa, Bernard, Biochemical Pharmacology, Prodrug Research: futile or fertile? 68 (2004) 2097-2106.
Ettmayer, Peter, Medicinal Chemistry, Lessons Learned from Marketed and Investigational Prodrugs, 47(10) (2004) 2394-2404.
Kobayashi, Yuichi, "New Reagent System for Attaining High Regio- and Stereoselectivities in Allylic Displacement of . . . " Organic Letters 7(2)(2005): 183-186.
Anthony D. Baxter, et al; "Synthesis and Use of 7-Substituted Norbornadienes t for the Preparation of Prostaglandins and Prostanoids" J. Chem. Soc. Perkin Trans. I 1986.
Silverman, Richard B., *The Organic Chemistry of Drug Design and Drug Action*, $2^{nd}$ Edition, Amsterdam: Elsevier Academic Press, 2004, p. 29.
Orlek et al. (J. Med. Chem. 1991, 34, 2726-2735).
Andersen et al. (Eur. J. Med. Chem. 1996, 31, 417-425).
Kohara et al. (J. Med. Chem. 1996, 39, 5228-5235).
Drysdale et al. (J. Med. Chem. 1992, 35, 2573-2581).
Remington's Pharmaceutical Sciences, Mack Publishing Company, Easton, Pa., 16th Edition, 1980.
Francis A. Carey, Organic Chemistry, New York: McGraw-Hill Book Company 1987, p. 63.
Chourasia and Jain in J Pharm Pharmaceut Sci 6 (1): 33-66, 2003.
Shareef et. al (AAPS PharmSci 2003; 5 (2) Article 17.

*Primary Examiner* — Joseph K. McKane
*Assistant Examiner* — Samantha Shterengarts
(74) *Attorney, Agent, or Firm* — Kevin J. Forrestal

(57) ABSTRACT

A compound having a structure

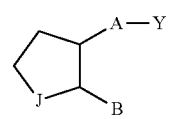

is disclosed herein. Compositions, medicaments, and therapeutic methods related thereto are also disclosed.

20 Claims, No Drawings

THERAPEUTIC COMPOUNDS

CROSS-REFERENCE TO RELATED APPLICATIONS

This application is a continuation of U.S. patent application Ser. No. 12/190,165, which is a continuation in part of U.S. patent application Ser. No. 11/742,987, which claims the benefit of U.S. Provisional Application No. 60/746,275, filed May 3, 2006, and Provisional Application No. 60/746,386, filed May 4, 2006, each of which is incorporated by reference in their entirety herein.

BACKGROUND

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

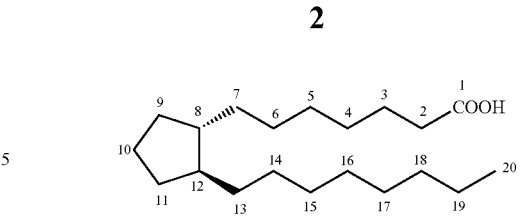

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

DESCRIPTION OF THE INVENTION

Disclosed herein is a compound having a structure

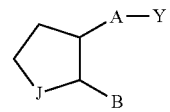

or a pharmaceutically acceptable salt thereof, or a prodrug thereof;
wherein Y is an organic acid functional group, or an amide or ester thereof comprising up to 14 carbon atoms; or Y is hydroxymethyl or an ether thereof comprising up to 14 carbon atoms; or Y is a tetrazolyl functional group;

A is —$(CH_2)_6$—, cis —$CH_2CH=CH-(CH_2)_3$—, or —$CH_2C\equiv C-(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O;

J is C=O, CHOH, CHF, CHCl, CHBr, $CF_2$, $CCl_2$, $CBr_2$, or CHCN; and

B is substituted aryl or substituted heteroaryl.

Also disclosed herein is a carboxylic acid or a bioisostere thereof, said carboxylic acid having a structure

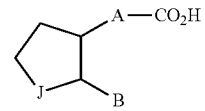

or a pharmaceutically acceptable salt thereof, or a prodrug thereof;
wherein A is —$(CH_2)_6$—, cis —$CH_2CH=CH-(CH_2)_3$—, or —$CH_2C\equiv C-(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O;

J is C=O, CHOH, CHF, CHCl, CHBr, $CF_2$, $CCl_2$, $CBr_2$, or CHCN; and

B is substituted aryl or substituted heteroaryl.

These compounds are useful for reducing intraocular pressure, treating glaucoma or intraocular pressure, growing hair, or improving the appearance of hair. Growing hair includes increasing the length or radius of individual hairs as well as increasing the number of hairs present in a given area.

Improving the appearance of hair includes improving the color, such as darkening, or improving its gloss, shine, or other properties related to the reflection or dispersion of light.

"Bioisosteres are substituents or groups that have chemical or physical similarities, and which produce broadly similar biological properties." Silverman, Richard B., *The Organic Chemistry of Drug Design and Drug Action*, 2$^{nd}$ Edition, Amsterdam: Elsevier Academic Press, 2004, p. 29.

While not intending to be limiting, organic acid functional groups are bioisoteres of carboxylic acids. An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Additionally, an amide or ester of one of the organic acids shown above comprising up to 14 carbon atoms is also contemplated. In an ester, a hydrocarbyl moiety replaces a hydrogen atom of an acid such as in a carboxylic acid ester, e.g. $CO_2Me$, $CO_2Et$, etc.

In an amide, an amine group replaces an OH of the acid. Examples of amides include $CON(R^2)_2$, $CON(OR^2)R^2$, $CON(CH_2CH_2OH)_2$, and $CONH(CH_2CH_2OH)$ where $R^2$ is independently H, $C_1$-$C_6$ alkyl, phenyl, or biphenyl. Moieties such as $CONHSO_2R^2$ are also amides of the carboxylic acid notwithstanding the fact that they may also be considered to be amides of the sulfonic acid $R^2$—$SO_3H$. The following amides are also specifically contemplated, $CONSO_2$-biphenyl, $CONSO_2$-phenyl, $CONSO_2$-heteroaryl, and $CONSO_2$-naphthyl. The biphenyl, phenyl, heteroaryl, or naphthyl may be substituted or unsubstituted.

Han et. al. (Biorganic & Medicinal Chemistry Letters 15 (2005) 3487-3490) has recently shown that the groups shown below are suitable bioisosteres for a carboxylic acid. The activity of compounds with these groups in inhibiting HCV NS3 protease was comparable to or superior to similar compounds where the group is replaced by $CO_2H$. Thus, Y could be any group depicted below.

Carboxylic Acid Bioisosteres According to Han et. al.

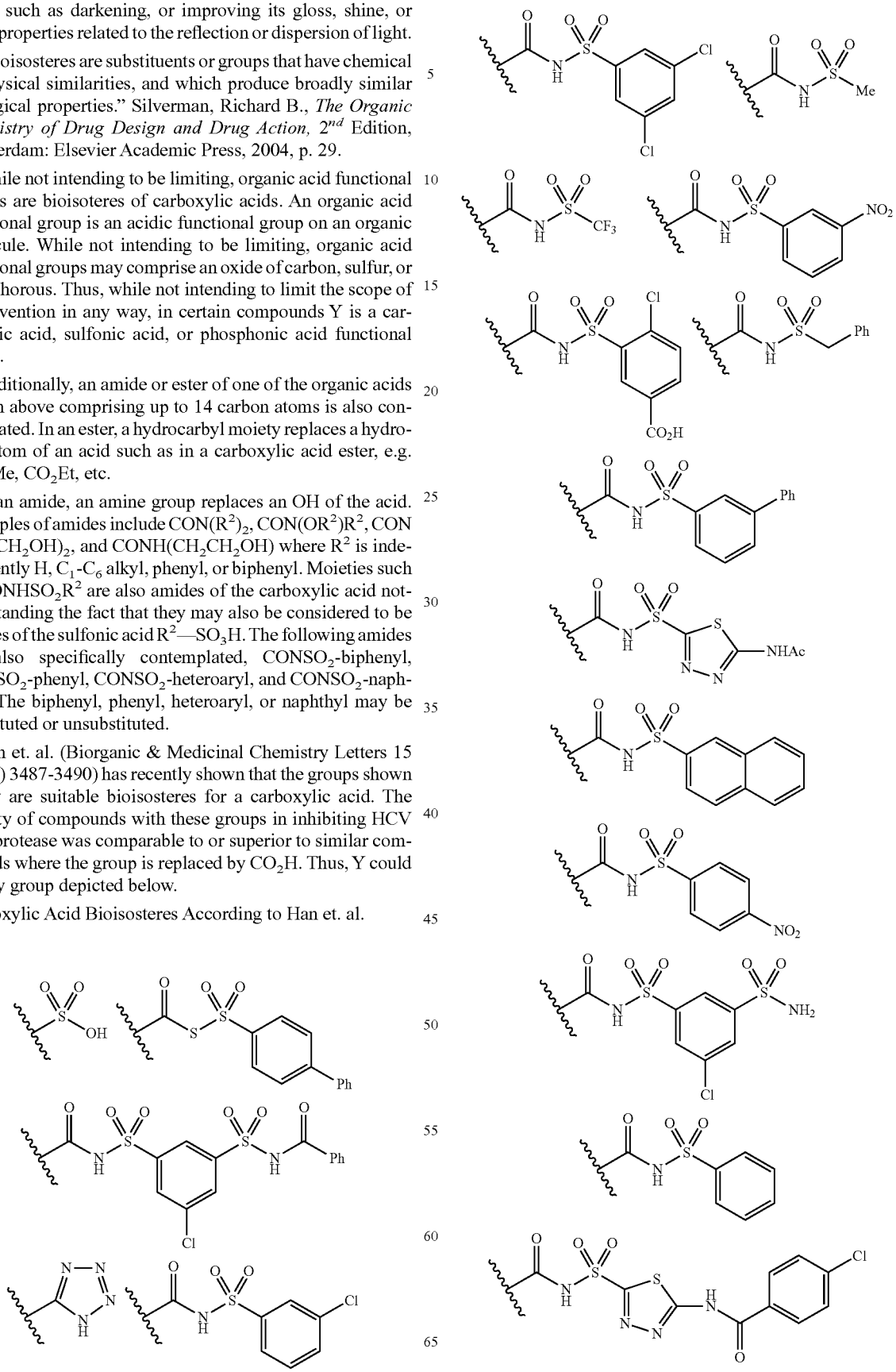

-continued

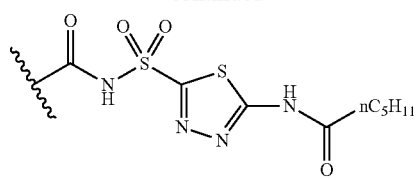

While not intending to limit the scope of the invention in any way, Y may also be hydroxymethyl or an ether thereof comprising up to 14 carbon atoms. An ether is a functional group wherein a hydrogen of an hydroxyl is replaced by carbon, e.g., Y is $CH_2OCH_3$, $CH_2OCH_2CH_3$, etc. These groups are also bioisosteres of a carboxylic acid.

"Up to 14 carbon atoms" means that the entire Y moiety, including the carbonyl carbon of a carboxylic acid ester or amide, and both carbon atoms in the —$CH_2O$—C of an ether has 0, 1, 2, 3, 4, 5, 6, 7, 8, 9, 10, 11, 12, 13, or 14 carbon atoms.

Finally, while not intending to limit the scope of the invention in any way, Y may be a tetrazolyl functional group.

While not intending to be limiting, examples of compounds having the identified Y are depicted below. In these examples R is H or hydrocarbyl, subject to the constraints defined herein. Each structure below represents a specific embodiment which is individually contemplated, as well as pharmaceutically acceptable salts and prodrugs of compounds which are represented by the structures. However, other examples are possible which may not fall within the scope of the structures shown below.

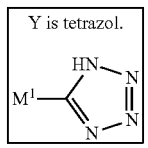

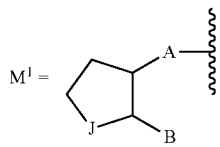

| Organic Acids | Esters | Amides |
|---|---|---|
| $M^1$—$CO_2H$ | $M^1$—$CO_2R$ | $M^1$—$CO_2NR_2$ |
| Carboxylic Acid | Carboxylic Acid Ester | Carboxylic Acid Amide |
| $M^1$—$P(O)(OH)_2$ | $M^1$—$P(O)(OH)R$ | $M^1$—$P(O)(OH)NR_2$ |
| Phosponic Acid | Phosphonic Acid Ester | Phosphonic Acid Amide |
| $M^1$—$SO_3H$ | $M^1$—$SO_3R$ | $M^1$—$SO_3NR_2$ |
| Sulfonic Acid | Sulfonic Acid Ester | Sulfonic Acid Amide |
| $M^1$—$CH_2OH$ | $M^1$—$CH_2OR$ | |
| Y is hydroxymethyl | Ether | |

A tetrazolyl functional group is another bioisostere of a carboxylic acid. An unsubstituted tetrazolyl functional group has two tautomeric forms, which can rapidly interconvert in aqueous or biological media, and are thus equivalent to one another. These tautomers are shown below.

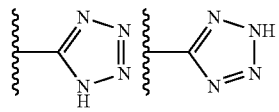

Additionally, if $R^2$ is $C_1$-$C_6$ alkyl, phenyl, or biphenyl, other isomeric forms of the tetrazolyl functional group such as the one shown below are also possible, unsubstituted and hydrocarbyl substituted tetrazolyl up to $C_{12}$ are considered to be within the scope of the term "tetrazolyl."

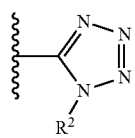

While not intending to limit the scope of the invention in any way, in one embodiment, Y is $CO_2R^2$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$,

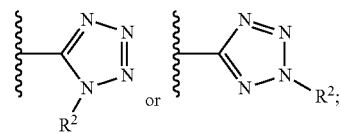

wherein $R^2$ is independently H, $C_1$-$C_6$ alkyl, unsubstituted phenyl, or unsubstituted biphenyl.

According to Silverman (p. 30), the moieties shown below are also bioisosteres of a carboxylic acid.

Carboxylic Acid Bioisosteres According to Silverman

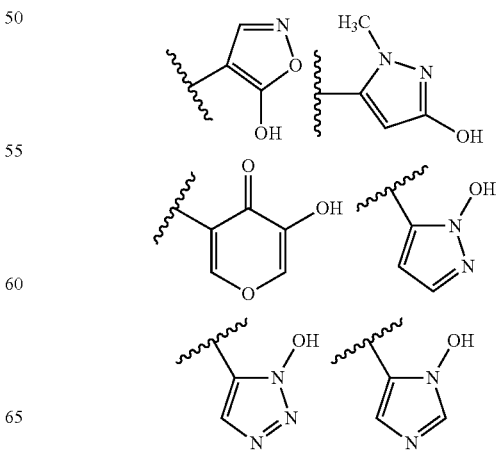

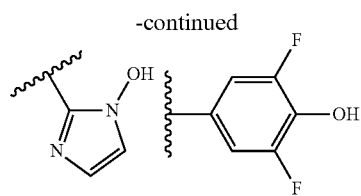

Orlek et al. (*J. Med. Chem.* 1991, 34, 2726-2735) described oxadiazoles as suitable bioisosteres for a carboxylic acid. These ester replacements were shown to be potent muscarinic agonists having improved metabolic stability. Oxadiazoles were also described by Anderson et al. (Eur. J. Med. Chem. 1996, 31, 417-425) as carboxamide replacements having improved in vivo efficacy at the benzodiazepine receptor.
Carboxylic Acid Bioisosteres According to Orlek et. al.

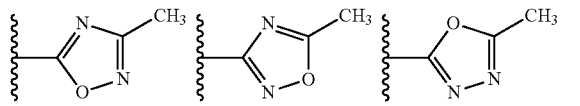

Kohara et al. (*J. Med. Chem.* 1996, 39, 5228-5235) described acidic heterocycles as suitable bioisosteres for a tetrazole. These carboxylic acid replacements were shown to be potent angiotensin II receptor antagonists having improved metabolic stability.
Tetrazole Bioisosteres According to Kohara et. al.

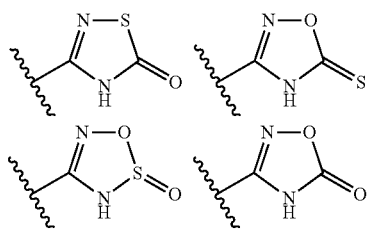

Drysdale et al. (*J. Med. Chem.* 1992, 35, 2573-2581) have described carboxylic acid mimics of non-peptide CCK-B receptor antagonists. The binding affinities of many of the bioisosteres are similar to the parent carboxylic acid.
Carboxylic Acid Bioisosteres According to Drysdale et. al.

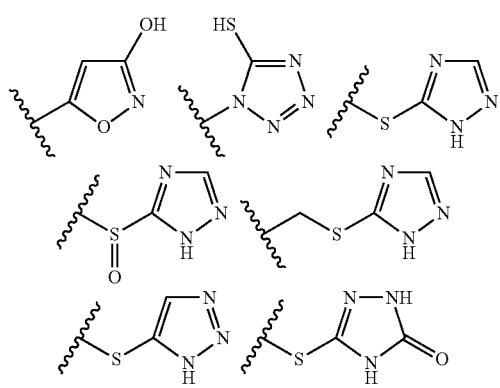

In relation to the identity of A disclosed in the chemical structures presented herein, A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be replaced with S or O; or A is —(CH$_2$)$_m$—Ar—(CH$_2$)$_o$— wherein Ar is interarylene or heterointerarylene, the sum of m and o is 1, 2, 3, or 4, and wherein one CH$_2$ may be replaced with S or O.

While not intending to be limiting, A may be —(CH$_2$)$_6$—, cis —CH$_2$CH═CH—(CH$_2$)$_3$—, or —CH$_2$C≡C—(CH$_2$)$_3$—.

Alternatively, A may be a group which is related to one of these three moieties in that any carbon is replaced with S and/or O. For example, while not intending to limit the scope of the invention in any way, A may be a moiety where S replaces one or two carbon atoms such as one of the following or the like.

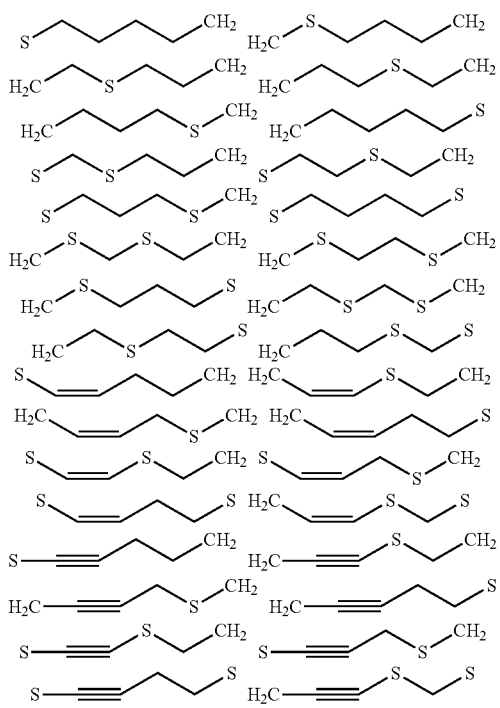

Alternatively, while not intending to limit the scope of the invention in any way, A may be a moiety where O replaces one or two carbon atoms such as one of the following or the like.

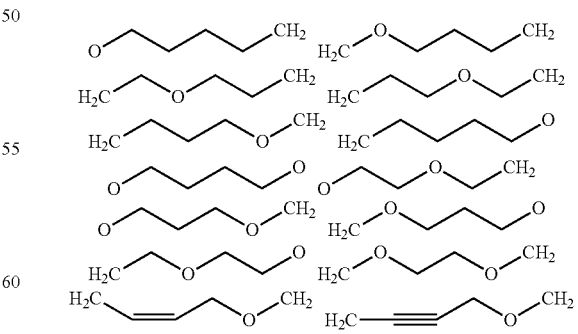

Alternatively, while not intending to limit the scope of the invention in any way, A may have an O replacing one carbon atom and an S replacing another carbon atom, such as one of the following or the like.

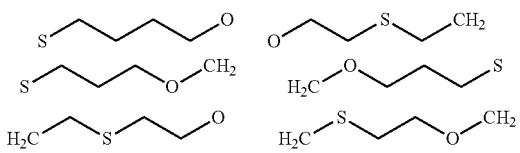

Alternatively, while not intending to limit the scope of the invention in any way, in certain embodiments A is —(CH$_2$)$_m$—Ar—(CH$_2$)$_o$— wherein Ar is interarylene or heterointerarylene, the sum of m and o is 1, 2, 3, or 4, and wherein one CH$_2$ may be replaced with S or O. In other words, while not intending to limit the scope of the invention in any way, in one embodiment A comprises 1, 2, 3, or 4 CH$_2$ moieties and Ar, e.g. —CH$_2$—Ar—, —(CH$_2$)$_2$—Ar—, —CH$_2$—Ar—CH$_2$—, —CH$_2$Ar—(CH$_2$)$_2$—, —(CH$_2$)$_2$—Ar—(CH$_2$)$_2$—, and the like;

in another embodiment A comprises: 0; 0, 1, 2, or 3 CH$_2$ moieties; and Ar, e.g., —O—Ar—, Ar—CH$_2$—O—, —O—Ar—(CH$_2$)$_2$—, —O—CH$_2$—Ar—, —O—CH$_2$—Ar—(CH$_2$)$_2$, and the like; or in another embodiment A comprises: S; 0, 1, 2, or 3 CH$_2$ moieties; and Ar, e.g., —S—Ar—, Ar—CH$_2$—S—, —S—Ar—(CH$_2$)$_2$—, —S—CH$_2$—Ar—, —S—CH$_2$—Ar—(CH$_2$)$_2$, —(CH$_2$)$_2$—S—Ar, and the like.

In another embodiment, the sum of m and o is 2, 3, or 4 wherein one CH$_2$ may be replaced with S or O.

In another embodiment, the sum of m and o is 3 wherein one CH$_2$ may be replaced with S or O.

In another embodiment, the sum of m and o is 2 wherein one CH$_2$ may be replaced with S or O.

In another embodiment, the sum of m and o is 4 wherein one CH$_2$ may be replaced with S or O.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —(CH$_2$)$_2$-Ph-. While not intending to limit scope of the invention in any way, substituents may have 4 or less heavy atoms, wherein the heavy atoms are C, N, O, S, P, F, Cl, Br, and/or I in any stable combination. Any number of hydrogen atoms required for a particular substituent will also be included. A substituent must be stable enough for the compound to be useful as described herein. In addition to the atoms listed above, a substituent may also have a metal cation or any other stable cation having an atom not listed above if the substituent is acidic and the salt form is stable. For example, —OH may form an —O$^-$Na$^+$ salt or CO$_2$H may form a CO$_2^-$K$^+$ salt. Any cation of the salt is not counted in the "4 or less heavy atoms." Thus, the substituent may be hydrocarbyl having up to 4 carbon atoms, including alkyl up to C$_4$, alkenyl, alkynyl, and the like;

hydrocarbyloxy up to C$_3$;

organic acid such as CO$_2$H, SO$_3$H, P(O)(OH)$_2$, and the like, and salts thereof;

CF$_3$;

halo, such as F, Cl, or Br;

hydroxyl;

NH$_2$ and alkylamine functional groups up to C$_3$;

other N or S containing substituents such as CN, NO$_2$, and the like;

and the like.

In one embodiment A is —(CH$_2$)$_m$—Ar—(CH$_2$)$_o$— wherein Ar is interphenylene, the sum of m and o is 1, 2, or 3, and wherein one CH$_2$ may be replaced with S or O.

In another embodiment A is —CH$_2$—Ar—OCH$_2$—. In another embodiment A is —CH$_2$—Ar—OCH$_2$— and Ar is interphenylene. In another embodiment, Ar is attached at the 1 and 3 positions, otherwise known as m-interphenylene, such as when A has the structure shown below.

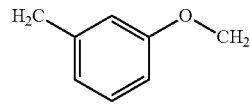

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph- wherein one CH$_2$ may be replaced with S or O.

In another embodiment A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph-.

In other embodiments, A has one of the following structures, where Y is attached to the aromatic or heteroaromatic ring.

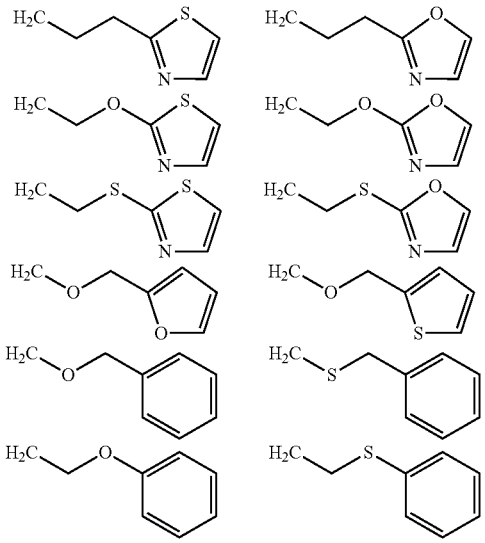

In another embodiment A is —CH$_2$OCH$_2$Ar.
In another embodiment A is —CH$_2$SCH$_2$Ar.

In another embodiment A is —(CH$_2$)$_3$Ar.
In another embodiment A is —CH$_2$O(CH$_2$)$_4$.
In another embodiment A is —CH$_2$S(CH$_2$)$_4$.
In another embodiment A is —(CH$_2$)$_6$—.
In another embodiment A is cis —CH$_2$CH═CH—(CH$_2$)$_3$—.
In another embodiment A is —CH$_2$C≡C—(CH$_2$)$_3$—.
In another embodiment A is —S(CH$_2$)$_3$S(CH$_2$)$_2$—.
In another embodiment A is —(CH$_2$)$_4$OCH$_2$—.
In another embodiment A is cis —CH$_2$CH═CH—CH$_2$OCH$_2$—.
In another embodiment A is —CH$_2$CH≡CH—CH$_2$OCH$_2$—.
In another embodiment A is —(CH$_2$)$_2$S(CH$_2$)$_3$—.
In another embodiment A is —CH$_2$-Ph-OCH$_2$—, wherein Ph is interphenylene.
In another embodiment A is —CH$_2$-mPh-OCH$_2$—, wherein mPh is m-interphenylene.
In another embodiment A is —CH$_2$—O—(CH2)$_4$—.
In another embodiment A is —CH$_2$—O—CH$_2$—Ar—, wherein Ar is 2,5-interthienylene.
In another embodiment A is —CH$_2$—O—CH$_2$—Ar—, wherein Ar is 2,5-interfurylene.
In another embodiment A is (3-methylphenoxy)methyl.
In another embodiment A is (4-but-2-ynyloxy)methyl.
In another embodiment A is 2-(2-ethylthio)thiazol-4-yl.
In another embodiment A is 2-(3-propyl)thiazol-5-yl.
In another embodiment A is 3-methoxymethyl)phenyl.
In another embodiment A is 3-(3-propylphenyl.
In another embodiment A is 3-methylphenethyl.
In another embodiment A is 4-(2-ethyl)phenyl.
In another embodiment A is 4-phenethyl.
In another embodiment A is 4-methoxybutyl.
In another embodiment A is 5-(methoxymethyl)furan-2-yl.
In another embodiment A is 5-(methoxymethyl)thiophen-2-yl.
In another embodiment A is 5-(3-propyl)furan-2-yl.
In another embodiment A is 5-(3-propyl)thiophen-2-yl.
In another embodiment A is 6-hexyl.
In another embodiment A is (Z)-6-hex-4-enyl.
In another embodiment, A is —(CH$_2$)$_3$Ar—, —O(CH$_2$)$_2$Ar—, —CH$_2$OCH$_2$Ar—, —(CH$_2$)$_2$OAr, —O(CH$_2$)$_2$Ar—, —CH$_2$OCH$_2$Ar—, or —(CH$_2$)$_2$OAr, wherein Ar is monocyclic interheteroarylene.
In another embodiment, Ar is interthienylene.
In another embodiment, Ar is interthiazolylene.
In another embodiment, Ar is interoxazolylene.

Compounds according to the each of the structures depicted below, and pharmaceutically acceptable salts thereof, and prodrugs thereof, are contemplated as individual embodiments. In other words, each structure represents a different embodiment.

$M^2 =$ [structure]

[structures with $M^2$ and Y]

-continued

[structures with $M^2$ and Y]

J is C═O, CHOH, CHF, CHCl, CHBr, or CHCN. Thus, each structure depicted below represents a compound embodiment which is individually contemplated. Pharmaceutically acceptable salts and prodrugs of compounds according to the structures below are also contemplated.

$M^3 =$ [structure A—Y, B]

$M^3$═O   $M^3$—Cl   $M^3$—F   $M^3$—OH   $M^3$—Br   $M^3$—CN $M^{3a} =$ [structure A—Y, B]

F\\$M^{3a}$/F   Cl\\$M^{3a}$/Cl   Br\\$M^{3a}$/Br

Aryl is an aromatic ring or ring system such as phenyl, naphthyl, biphenyl, and the like.

Heteroaryl is aryl having one or more N, O, or S atoms in the ring, i.e. one or more ring carbons are substituted by N, O, and/or S. While not intending to be limiting, examples of heteroaryl include thienyl, pyridinyl, furyl, benzothienyl, benzofuryl, imidizololyl, indolyl, and the like.

A substituent of aryl or heteroaryl may have up to 20 non-hydrogen atoms each in any stable combination and as many hydrogen atoms as necessary, wherein the non-hydrogen atoms are C, N, O, S, P, F, Cl, Br, and/or I in any stable combination. However, the total number of non-hydrogen atoms on all of the substituents combined must also be 20 or less. A substituent must be sufficiently stable for the compound to be useful as described herein. In addition to the atoms listed above, a substituent may also have a metal cation or other stable cation having an atom not listed above if the substituent is acidic and the salt form is stable. For example, —OH may form an —O$^-$Na$^+$ salt or CO$_2$H may form a CO$_2^-$K$^+$ salt. Thus, while not intending to limit the scope of the invention in any way, a substituent may be:

hydrocarbyl, i.e. a moiety consisting of only carbon and hydrogen such as alkyl, alkenyl, alkynyl, and the like, including linear, branched or cyclic hydrocarbyl, and combinations thereof;

hydrocarbyloxy, meaning O-hydrocarbyl such as OCH$_3$, OCH$_2$CH$_3$, O-cyclohexyl, etc, up to 19 carbon atoms;

other ether substituents such as CH$_2$OCH$_3$, (CH$_2$)$_2$OCH(CH$_3$)$_2$, and the like;

thioether substituents including S-hydrocarbyl and other thioether substituents;

hydroxyhydrocarbyl, meaning hydrocarbyl-OH such as CH$_2$OH, C(CH$_3$)$_2$OH, etc, up to 19 carbon atoms;

nitrogen substituents such as NO$_2$, CN, and the like, including amino, such as NH$_2$, NH(CH$_2$CH$_3$OH), NHCH$_3$, and the like up to 19 carbon atoms;

carbonyl substituents, such as CO$_2$H, ester, amide, and the like;

halogen, such as chloro, fluoro, bromo, and the like fluorocarbyl, such as CF$_3$, CF$_2$CF$_3$, etc.;

phosphorous substituents, such as PO$_3^{2-}$, and the like;

sulfur substituents, including S-hydrocarbyl, SH, SO$_3$H, SO$_2$-hydrocarbyl, SO$_3$-hydrocarbyl, and the like.

Substituted aryl or heteroaryl may have as many substituents as the ring or ring system will bear, and the substituents may be the same or different. Thus, for example, an aryl ring or a heteroaryl ring may be substituted with chloro and methyl; methyl, OH, and F; CN, NO$_2$, and ethyl; and the like including any conceivable substituent or combination of substituent possible in light of this disclosure.

Substituted aryl or substituted heteroaryl also includes a bicyclic or polycyclic ring system wherein one or more rings are aromatic and one or more rings are not. For example, indanonyl, indanyl, indanolyl, tetralonyl, and the like are substituted aryl. For this type of polycyclic ring system, an aromatic or heteroaromatic ring, not a non-aromatic ring, must be attached to the remainder of the molecule. In other words, in any structure depicting —B herein, where — is a bond, the bond is a direct bond to an aromatic ring.

In one embodiment, B is substituted aryl or heteroaryl.

In another embodiment B is substituted phenyl.

In another embodiment B has no halogen atoms.

In another embodiment B is 4-(1-hydroxy-2,2-dimethylpropyl)phenyl.

In another embodiment B is 4-(1-hydroxy-2-methylpropan-2-yl)phenyl.

In another embodiment B is 4-(1-hydroxy-2-methylpropyl)phenyl.

In another embodiment B is 4-(1-hydroxybutyl)phenyl.

In another embodiment B is 4-(1-hydroxyheptyl)phenyl.

In another embodiment B is 4-(1-hydroxyhexyl)phenyl.

In another embodiment B is 4-(1-hydroxypentyl)phenyl.

In another embodiment B is 4-(1-hydroxypropyl)phenyl.

In another embodiment B is 4-(3-hydroxy-2-methylheptan-2-yl)phenyl.

In another embodiment B is 4-(3-hydroxy-2-methyloctan-2-yl)phenyl.

In another embodiment B is 1-hydroxy-2,3-dihydro-1H-inden-5-yl.

In another embodiment B is 2,3-dihydro-1H-inden-5-yl.

In another embodiment B is 3-(hydroxy(1-propylcyclobutyl)methyl)phenyl.

In another embodiment B is 4-(1-hydroxy-5,5-dimethylhexyl)phenyl.

In another embodiment B is 4-(hydroxy(1-propylcyclobutyl)methyl)phenyl.

In another embodiment B is 4-tert-butylphenyl.

In another embodiment B is 4-hexylphenyl.

In another embodiment B is 4-(1-hydroxy-2-phenylethyl)phenyl.

In another embodiment B is 4-(1-hydroxy-3-phenylpropyl)phenyl.

In another embodiment B is 4-(1-hydroxycyclobutyl)phenyl.

In another embodiment B is 4-(2-cyclohexyl-1-hydroxyethyl)phenyl.

In another embodiment B is 4-(3-cyclohexyl-1-hydroxypropyl)phenyl.

In another embodiment B is 4-(cyclohexyl(hydroxy)methyl)phenyl.

In another embodiment B is 4-(cyclohexylmethyl)phenyl.

In another embodiment B is 4-(hydroxy(phenyl)methyl)phenyl.

Another embodiment is a compound according to the structure

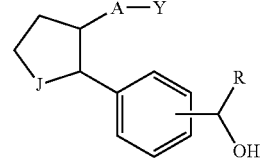

or a pharmaceutical salt thereof, or a prodrug thereof, wherein R is hydrogen or C$_{1-10}$ hydrocarbyl.

Another embodiment is a compound according to the structure

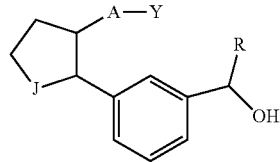

or a pharmaceutical salt thereof, or a prodrug thereof, wherein R is hydrogen or C$_{1-10}$ hydrocarbyl.

Another embodiment is a compound according to the structure

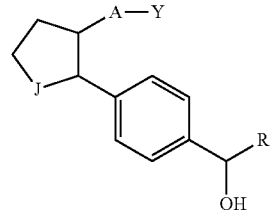

or a pharmaceutical salt thereof, or a prodrug thereof, wherein R is hydrogen or $C_{1-10}$ hydrocarbyl.

Another embodiment is a compound according to the structure

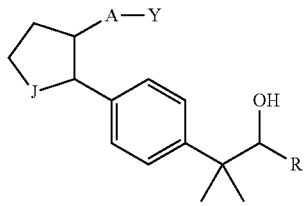

"C1-10" hydrocarbyl is hydrocarbyl having 1, 2, 3, 4, 5, 6, 7, 8, 9, or 10 carbon atoms.

Hydrocarbyl is a moiety consisting of only carbon and hydrogen, and includes, but is not limited to alkyl, alkenyl, alkynyl, and the like, and in some cases aryl, and combinations thereof.

Alkyl is hydrocarbyl having no double or triple bonds including:

linear alkyl such as methyl, ethyl, propyl, n-butyl, n-pentyl, n-hexyl, and the like;

branched alkyl such as isopropyl, branched butyl isomers (i.e. sec-butyl, tert-butyl, etc), branched pentyl isomers (i.e. isopentyl, etc), branched hexyl isomers, and higher branched alkyl fragments;

cycloalkyl such as cyclopropyl, cyclobutyl, cyclopentyl, cyclohexyl, cycloheptyl, etc.; and alkyl fragments consisting of both cyclic and noncyclic components, whether linear or branched, which may be attached to the remainder of the molecule at any available position including terminal, internal, or ring carbon atoms.

Alkenyl is hydrocarbyl having one or more double bonds including linear alkenyl, branched alkenyl, cyclic alkenyl, and combinations thereof in analogy to alkyl.

Alkynyl is hydrocarbyl having one or more triple bonds including linear alkynyl, branched alkynyl, cyclic alkynyl and combinations thereof in analogy to alkyl.

Aryl is an unsubstituted or substituted aromatic ring or ring system such as phenyl, naphthyl, biphenyl, and the like. Aryl may or may not be hydrocarbyl, depending upon whether it has substituents with heteroatoms.

Arylalkyl is alkyl which is substituted with aryl. In other words alkyl connects aryl to the remaining part of the molecule. Examples are —CH$_2$-Phenyl, —CH$_2$—CH$_2$-Phenyl, and the like. Arylalkyl may or may not be hydrocarbyl, depending upon whether it has substituents with heteroatoms. Unconjugated dienes or polyenes have one or more double bonds which are not conjugated. They may be linear, branched, or cyclic, or a combination thereof.

Combinations of the above are also possible.

Thus, each of the structures below is contemplated. These structures, or pharmaceutically acceptable salts thereof, or prodrugs thereof, individually represent a compound which is an embodiment contemplated herein. In other words, each structure represents a different embodiment.

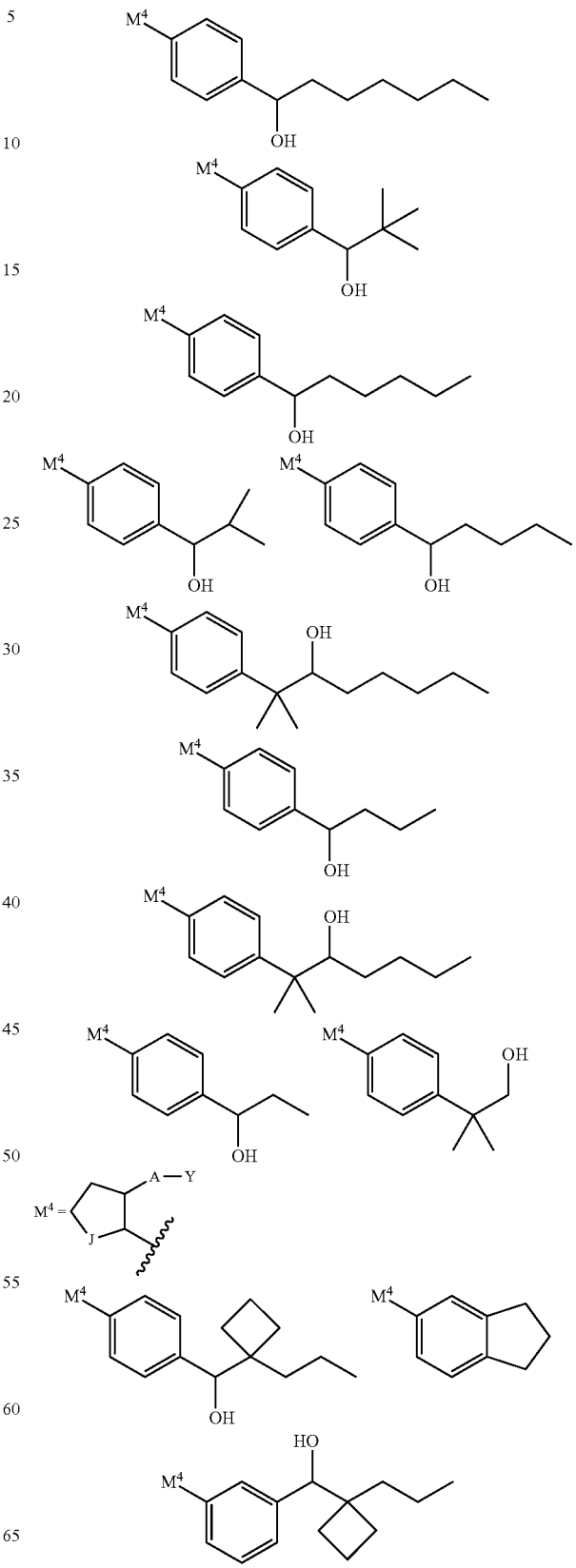

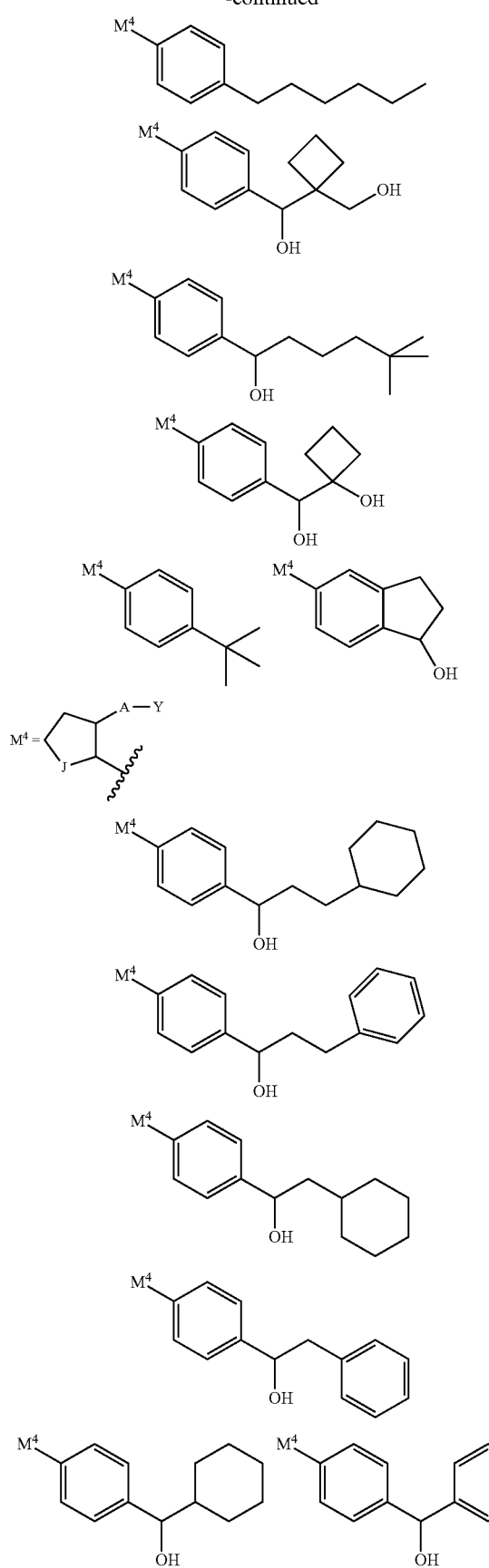
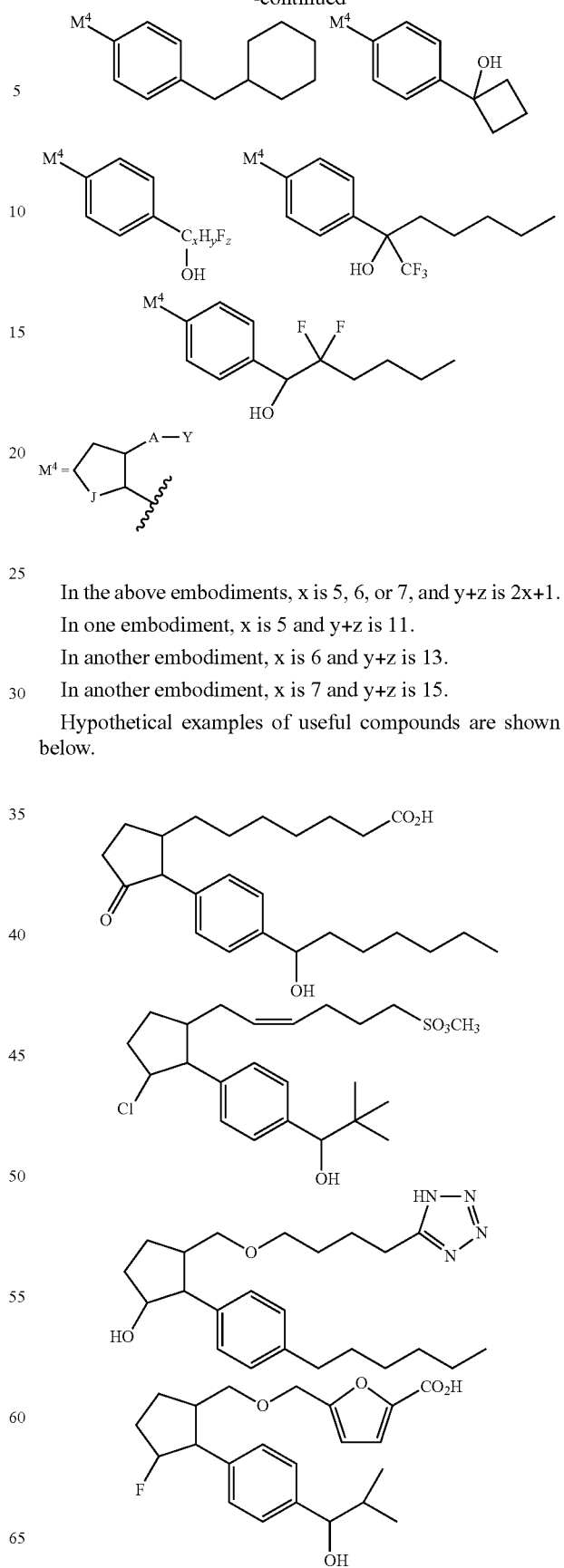
In the above embodiments, x is 5, 6, or 7, and y+z is 2x+1.
In one embodiment, x is 5 and y+z is 11.
In another embodiment, x is 6 and y+z is 13.
In another embodiment, x is 7 and y+z is 15.
Hypothetical examples of useful compounds are shown below.

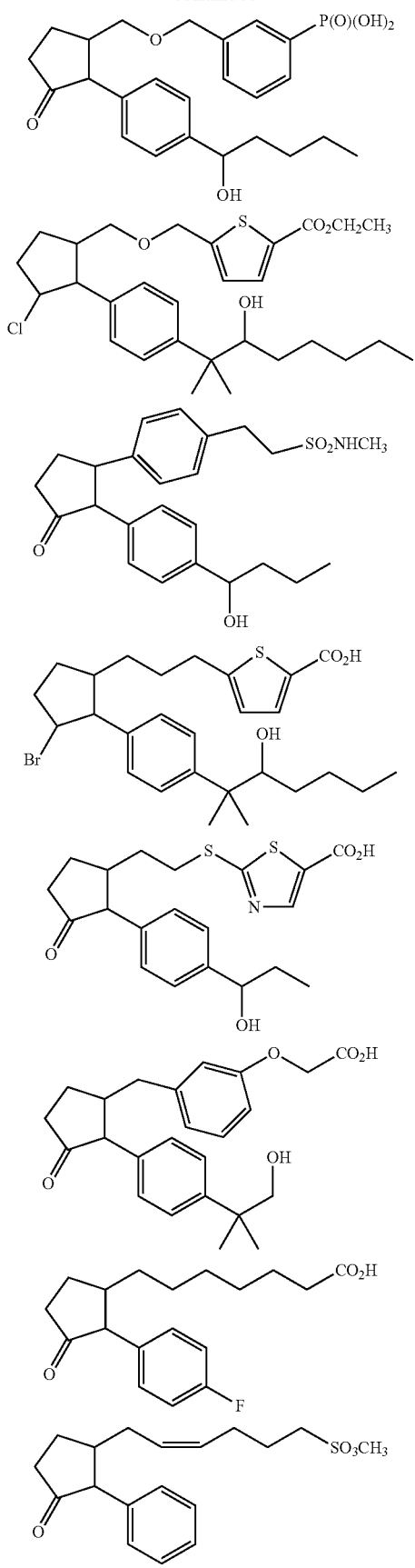
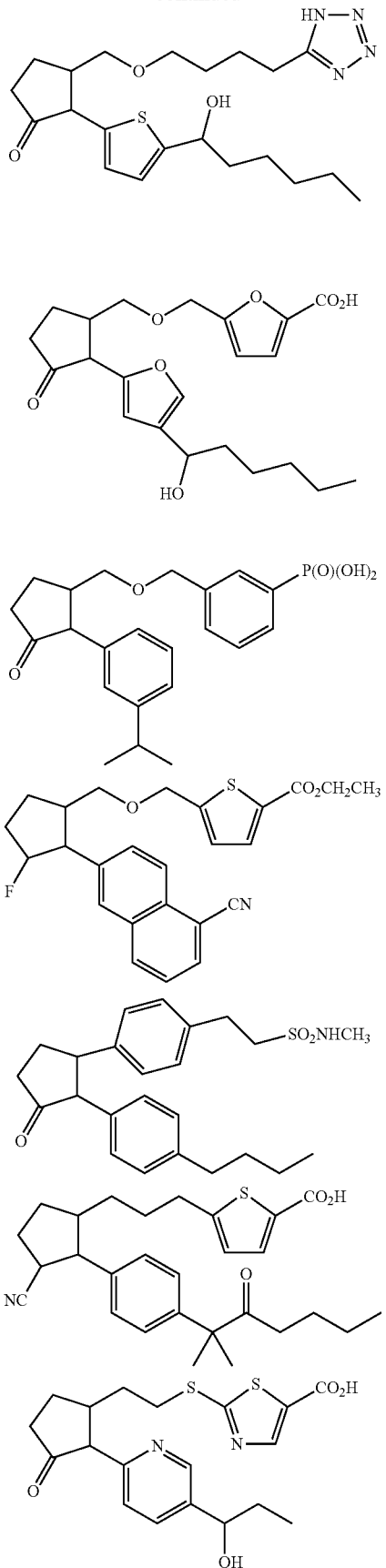

-continued

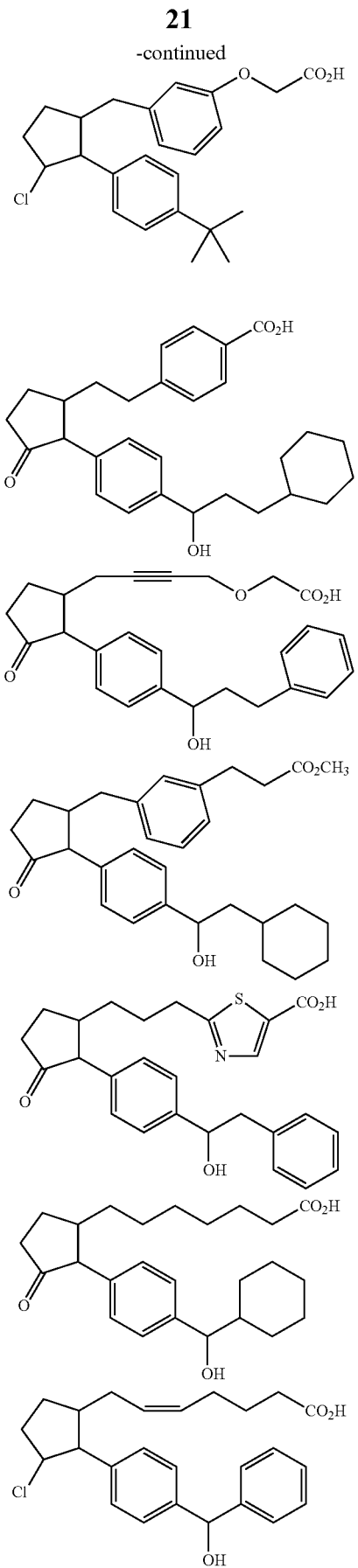

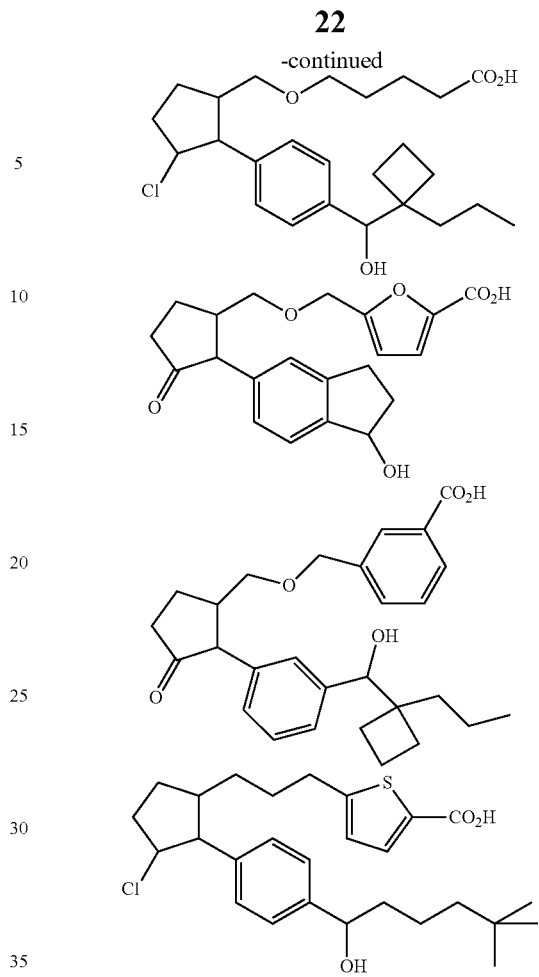

The following compounds are also useful:
5-(3-{(1S,2S)-2-[4-(1-Hydroxy-hexyl)-phenyl]-3-oxo-cyclopentyl}-propyl)-thiophene-2-carboxylic acid (9);
5-(3-{(1S,2S)-2-[4-(1-Hydroxy-hexyl)-phenyl]-3-oxo-cyclopentyl}-propyl)-thiophene-2-carboxylic acid methyl ester (8);
5-(3-{(1S,2S)-2-[4-(1-Hydroxy-hexyl)-phenyl]-3-oxo-cyclopentyl}-propyl)-thiophene-2-carboxylic acid isopropyl ester (10);
5-(3-{(1S,2S)-2-[4-((R)-1-Hydroxy-hexyl)-phenyl]-3-oxo-cyclopentyl}-propyl)-thiophene-2-carboxylic acid;
5-(3-{(1S,2S)-2-[4-((R)-1-Hydroxy-hexyl)-phenyl]-3-oxo-cyclopentyl}-propyl)-thiophene-2-carboxylic acid methyl ester;
5-(3-{(1S,2S)-2-[4-((R)-1-Hydroxy-hexyl)-phenyl]-3-oxo-cyclopentyl}-propyl)-thiophene-2-carboxylic acid isopropyl ester;
5-(3-{(1S,2S)-2-[4-((S)-1-Hydroxy-hexyl)-phenyl]-3-oxo-cyclopentyl}-propyl)-thiophene-2-carboxylic acid;
5-(3-{(1S,2S)-2-[4-((S)-1-Hydroxy-hexyl)-phenyl]-3-oxo-cyclopentyl}-propyl)-thiophene-2-carboxylic acid methyl ester;
5-(3-{(1S,2S)-2-[4-((S)-1-Hydroxy-hexyl)-phenyl]-3-oxo-cyclopentyl}-propyl)-thiophene-2-carboxylic acid isopropyl ester;
5-(3-{(1S,2S)-3,3-Dichloro-2-[4-(1-hydroxy-hexyl)-phenyl]-cyclopentyl}-propyl)-thiophene-2-carboxylic acid (13);
5-(3-{(1S,2S)-3,3-Dichloro-2-[4-(1-hydroxy-hexyl)-phenyl]-cyclopentyl}-propyl)-thiophene-2-carboxylic acid methyl ester (12);

(Z)-7-{(1S,5S)-5-[4-(1-Hydroxy-hexyl)-phenyl]-4-oxo-cyclopent-2-enyl}-hept-5-enoic acid (17);
(Z)-7-{(1S,5S)-5-[4-(1-Hydroxy-hexyl)-phenyl]-4-oxo-cyclopent-2-enyl}-hept-5-enoic acid isopropyl ester;
(Z)-7-{(1R,2S)-2-[4-(1-Hydroxy-hexyl)-phenyl]-3-oxo-cyclopentyl}-hept-5-enoic acid (19);
(Z)-7-{(1R,2S)-2-[4-(1-Hydroxy-hexyl)-phenyl]-3-oxo-cyclopentyl}-hept-5-enoic acid isopropyl ester;
(Z)-7-{(1R,2S,3R)-3-Chloro-2-[4-(1-hydroxy-hexyl)-phenyl]-cyclopentyl}-hept-5-enoic acid (22);
(Z)-7-{(1R,2S,3R)-3-Chloro-2-[4-(1-hydroxy-hexyl)-phenyl]-cyclopentyl}-hept-5-enoic acid isopropyl ester;
(Z)-7-{(1R,2S,3R)-3-Hydroxy-2-[4-(1-hydroxy-hexyl)-phenyl]-cyclopentyl}-hept-5-enoic acid (25);
(Z)-7-{(1R,2S,3R)-3-Hydroxy-2-[4-(1-hydroxy-hexyl)-phenyl]-cyclopentyl}-hept-5-enoic acid isopropyl ester;
(Z)-7-{(1R,2S,3S)-3-Chloro-2-[4-(1-hydroxy-hexyl)-phenyl]-cyclopentyl}-hept-5-enoic acid (27); and
(Z)-7-{(1R,2S,3S)-3-Chloro-2-[4-(1-hydroxy-hexyl)-phenyl]-cyclopentyl}-hept-5-enoic acid isopropyl ester.

COMPOUND EXAMPLES

The following are hypothetical examples of useful compounds:

Compound Example 1

A compound having a structure

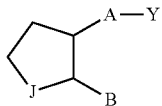

or a pharmaceutically acceptable salt thereof, or a prodrug thereof;
wherein Y is an organic acid functional group, or an amide or ester thereof comprising up to 14 carbon atoms; or Y is hydroxymethyl or an ether thereof comprising up to 14 carbon atoms; or Y is a tetrazolyl functional group;
A is —$(CH_2)_6$—, cis —$CH_2CH=CH—(CH_2)_3$—, or —$CH_2C\equiv C—(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O;
J is C=O, CHOH, CHF, CHCl, CHBr, $CF_2$, $CCl_2$, $CBr_2$, or CHCN; and
B is substituted aryl or substituted heteroaryl.

Compound Example 2

The compound according to compound example 1 wherein Y is selected from $CO_2R^2$, $CON(R^2)_2$, CON($OR^2$)$R^2$, $CON(CH_2CH_2OH)_2$, CONH($CH_2CH_2OH$), $CH_2OH$, $P(O)(OH)_2$, $CONHSO_2R^2$, $SO_2N(R^2)_2$, $SO_2NHR^2$,

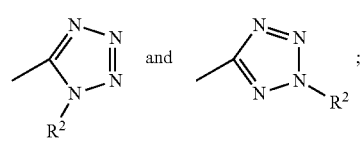

wherein $R^2$ is independently H, $C_1$-$C_6$ alkyl, unsubstituted phenyl, or unsubstituted biphenyl.

Compound Example 3

The compound according to compound example 1 or 2 wherein B is substituted phenyl.

Compound Example 4

The compound according to compound example 1 or 2 having a structure

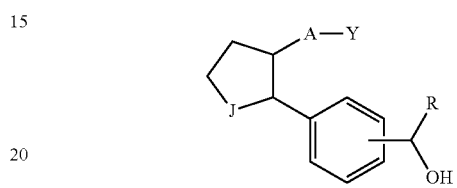

or a pharmaceutically acceptable salt thereof, or a prodrug thereof;
R is hydrogen or $C_{1-10}$ hydrocarbyl.

Compound Example 5

The compound according to compound example 4 wherein R is alkyl.

Compound Example 6

The compound according to compound example 4 wherein R is arylalkyl.

Compound Example 7

The compound according to compound example any one of compound examples 1 to 6 having a structure

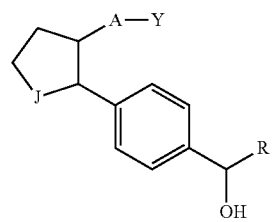

or a pharmaceutically acceptable salt thereof, or a prodrug thereof;
R is hydrogen or $C_{1-10}$ hydrocarbyl.

Compound Example 8

The compound according to compound example 1 or 2 wherein A is (3-methylphenoxy)methyl.

Compound Example 9

The compound according to compound example 1 or 2 wherein A is (4-but-2-ynyloxy)methyl.

Compound Example 10

The compound according to compound example 1 or 2 wherein A is 2-(2-ethylthio)thiazol-4-yl.

Compound Example 11

The compound according to compound example 1 or 2 wherein A is 2-(3-propyl)thiazol-5-yl.

Compound Example 12

The compound according to compound example 1 or 2 wherein A is 3-methoxymethyl)phenyl.

Compound Example 13

The compound according to compound example 1 or 2 wherein A is 3-(3-propylphenyl.

Compound Example 14

The compound according to compound example 1 or 2 wherein A is 3-methylphenethyl.

Compound Example 15

The compound according to compound example 1 or 2 wherein A is 4-(2-ethyl)phenyl.

Compound Example 16

The compound according to compound example 1 or 2 wherein A is 4-phenethyl.

Compound Example 17

The compound according to compound example 1 or 2 wherein A is 4-methoxybutyl.

Compound Example 18

The compound according to compound example 1 or 2 wherein A is 5-(methoxymethyl)furan-2-yl.

Compound Example 19

The compound according to compound example 1 or 2 wherein A is 5-(methoxymethyl)thiophen-2-yl.

Compound Example 20

The compound according to compound example 1 or 2 wherein A is 5-(3-propyl)furan-2-yl.

Compound Example 21

The compound according to compound example 1 or 2 wherein A is 5-(3-propyl)thiophen-2-yl.

Compound Example 22

The compound according to compound example 1 or 2 wherein A is 6-hexyl.

Compound Example 23

The compound according to compound example 1 or 2 wherein A is (Z)-6-hex-4-enyl.

Compound Example 24

The compound according to any one of compound examples 1, 2, and 8-23 wherein B is 4-(1-hydroxy-2,2-dimethylpropyl)phenyl.

Compound Example 25

The compound according to any one of compound examples 1, 2, and 8-23 wherein B is 4-(1-hydroxy-2-methylpropan-2-yl)phenyl.

Compound Example 26

The compound according to any one of compound examples 1, 2, and 8-23 wherein B is 4-(1-hydroxy-2-methylpropyl)phenyl.

Compound Example 27

The compound according to any one of compound examples 1, 2, and 8-23 wherein B is 4-(1-hydroxybutyl)phenyl.

Compound Example 28

The compound according to any one of compound examples 1, 2, and 8-23 wherein B is 4-(1-hydroxyheptyl)phenyl.

Compound Example 29

The compound according to any one of compound examples 1, 2, and 8-23 wherein B is 4-(1-hydroxyhexyl)phenyl.

Compound Example 30

The compound according to any one of compound examples 1, 2, and 8-23 wherein B is 4-(1-hydroxypentyl)phenyl.

Compound Example 31

The compound according to any one of compound examples 1, 2, and 8-23 wherein B is 4-(1-hydroxypropyl)phenyl.

Compound Example 32

The compound according to any one of compound examples 1, 2, and 8-23 wherein B is 4-(3-hydroxy-2-methylheptan-2-yl)phenyl.

Compound Example 33

The compound according to any one of compound examples 1, 2, and 8-23 wherein B is 4-(3-hydroxy-2-methyloctan-2-yl)phenyl.

Compound Example 34

The compound according to any one of compound examples 1, 2, and 8-23 wherein B is 1-hydroxy-2,3-dihydro-1H-inden-5-yl.

Compound Example 35

The compound according to any one of compound examples 1, 2, and 8-23 wherein B is 2,3-dihydro-1H-inden-5-yl.

Compound Example 36

The compound according to any one of compound examples 1, 2, and 8-23 wherein B is 3-(hydroxy(1-propyl-cyclobutyl)methyl)phenyl.

Compound Example 37

The compound according to any one of compound examples 1, 2, and 8-23 wherein B is 4-(1-hydroxy-5,5-dimethylhexyl)phenyl.

Compound Example 38

The compound according to any one of compound examples 1, 2, and 8-23 wherein B is 4-(hydroxy(1-propyl-cyclobutyl)methyl)phenyl.

Compound Example 39

The compound according to any one of compound examples 1, 2, and 8-23 wherein B is 4-tert-butylphenyl.

Compound Example 40

The compound according to any one of compound examples 1, 2, and 8-23 wherein B is 4-hexylphenyl.

Compound Example 41

The compound according to any one of compound examples 1, 2, and 8-23 wherein B is 4-(1-hydroxy-2-phenylethyl)phenyl.

Compound Example 42

The compound according to any one of compound examples 1, 2, and 8-23 wherein B is 4-(1-hydroxy-3-phenylpropyl)phenyl.

Compound Example 43

The compound according to any one of compound examples 1, 2, and 8-23 wherein B is 4-(1-hydroxycyclobutyl)phenyl.

Compound Example 44

The compound according to any one of compound examples 1, 2, and 8-23 wherein B is 4-(2-cyclohexyl-1-hydroxyethyl)phenyl.

Compound Example 45

The compound according to any one of compound examples 1, 2, and 8-23 wherein B is 4-(3-cyclohexyl-1-hydroxypropyl)phenyl.

Compound Example 46

The compound according to any one of compound examples 1, 2, and 8-23 wherein B is 4-(cyclohexyl(hydroxy)methyl)phenyl.

Compound Example 47

The compound according to any one of compound examples 1, 2, and 8-23 wherein B is 4-(cyclohexylmethyl)phenyl.

Compound Example 48

The compound according to any one of compound examples 1, 2, and 8-23 wherein B is 4-(hydroxy(phenyl)methyl)phenyl.

The following are hypothetical examples of compositions, kits, methods, uses, and medicaments employing the hypothetical compound examples.

Composition Example

A composition comprising a compound according to any one of compound examples 1 to 48, wherein said composition is a liquid which is ophthalmically acceptable.

Medicament Examples

Use of a compound according to any one of compound examples 1 to 48 in the manufacture of a medicament for the treatment of glaucoma or ocular hypertension in a mammal.

A medicament comprising a compound according to any one of compound examples 1 to 48, wherein said composition is a liquid which is ophthalmically acceptable.

Method Example

A method comprising administering a compound according to any one of compound examples 1 to 48 to a mammal for the treatment of glaucoma or ocular hypertension.

Kit Example

A kit comprising a composition comprising compound according to any one of compound examples 1 to 48, a container, and instructions for administration of said composition to a mammal for the treatment of glaucoma or ocular hypertension.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds may be in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including
non-selective adrenergic agonists such as epinephrine borate, epinephrine hydrochloride, and dipivefrin, and the like, or pharmaceutically acceptable salts or prodrugs thereof; and
$\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including
direct acting cholinergic agonists such as carbachol, pilocarpine hydrochloride, pilocarbine nitrate, pilocarpine, and the like, or pharmaceutically acceptable salts or prodrugs thereof;
chlolinesterase inhibitors such as demecarium, echothiophate, physostigmine, and the like, or pharmaceutically acceptable salts or prodrugs thereof;
Glutamate Antagonists and other neuroprotective agents such as $Ca^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;
Prostamides such as bimatoprost, or pharmaceutically acceptable salts or prodrugs thereof; and
Prostaglandins including travoprost, UFO-21, chloprostenol, fluprostenol, 13,14-dihydro-chloprostenol, isopropyl unoprostone, latanoprost and the like.
Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art.

In addition to the treatment of glaucoma, prostaglandin EP2 selective agonists are believed to have several medical uses. For example, U.S. Pat. No. 6,437,146 teaches the use of prostaglandin EP2 selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No. 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

These compounds can also be used to treat or prevent conditions affecting the posterior part of the eye including maculopathies/retinal degeneration such as non-exudative age related macular degeneration (ARMD), exudative age related macular degeneration (ARMD), choroidal neovascularization, diabetic retinopathy, acute macular neuroretinopathy, central serous chorioretinopathy, cystoid macular edema, and diabetic macular edema; uveitis/retinitis/choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasucular diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigement epitheliitis. Preferably, the disease or condition is retinitis pigmentosa, proliferative vitreal retinopathy (PVR), age-related macular degeneration (ARMD), diabetic retinopathy, diabetic macular edema, retinal detachment, retinal tear, uveitus, or cytomegalovirus retinitis.

These compounds are also useful in treating asthma.

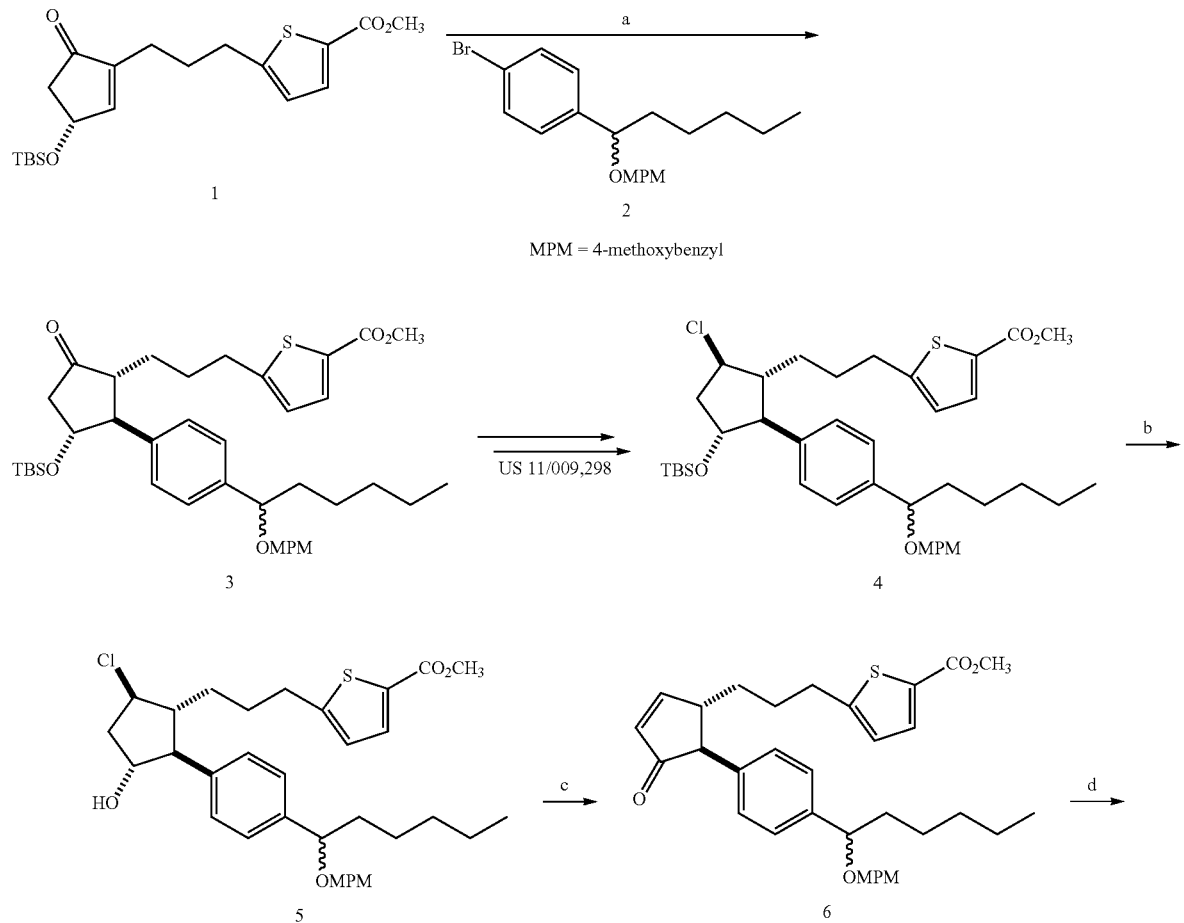

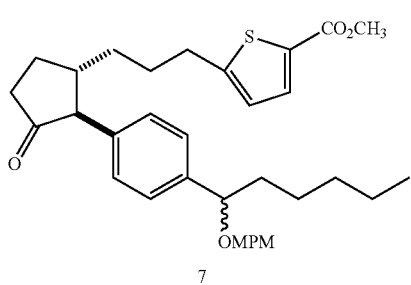

7

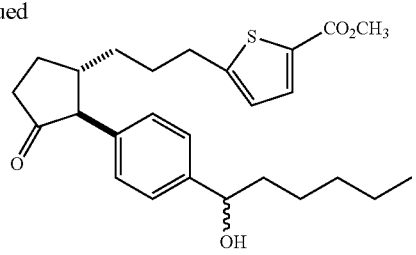

8

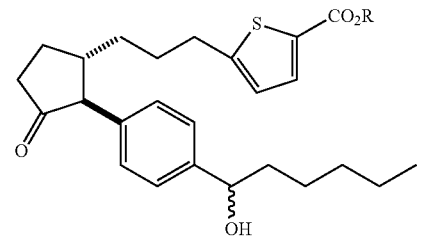

9, R = H
10, R = iPr

Conditions: (a) 2, tert-BuLi, THF -78° C.; 2-thienylCuCNLi, 1; (b) HF•pyridine, CH₃CN, 0° C.; (c) Swern [O]; (d) [Ph₃PCuH]₆; (e) DDQ; (f) aq. LiOH, THF 60° C.; (g) iPrI, DBU, acetone.

5-[3-((1R,2S,3R)-3-(tert-Butyl-dimethyl-silanyloxy)-2-{4-[1-(4-methoxy-benzyloxy)-hexyl]-phenyl}-5-oxo-cyclopentyl)-propyl]-thiophene-2-carboxylic acid methyl ester (3). The synthesis of compound 3 was described in U.S. Provisional Patent Application No. 60/744,236, filed on Apr. 4, 2006, which is expressly incorporated by reference herein.

5-[3-((1R,2S,3R,5R)-3-(tert-Butyl-dimethyl-silanyloxy)-5-chloro-2-{4-[1-(4-methoxy-benzyloxy)-hexyl]-phenyl}-cyclopentyl)-propyl]-thiophene-2-carboxylic acid methyl ester (4). Conversion of 3→4 was accomplished with an analogous procedure to one described in U.S. patent application Ser. No. 11/009,298, filed on Dec. 10, 2004, which is expressly incorporated by reference herein.

5-[3-((1R,2S,3R,5R)-5-Chloro-3-hydroxy-2-{4-[1-(4-methoxy-benzyloxy)-hexyl]-phenyl}-cyclopentyl)-propyl]-thiophene-2-carboxylic acid methyl ester (5). Compound 5 was prepared using the standard HF-pyridine procedure described in U.S. patent application Ser. No. 11/009,298.

5-[3-((1S,5S)-5-{4-[1-(4-Methoxy-benzyloxy)-hexyl]-phenyl}-4-oxo-cyclopent-2-enyl)-propyl]-thiophene-2-carboxylic acid methyl ester (6). A solution of DMSO (120 μL, 1.69 mmol) in 1 mL CH₂Cl₂ was added to a −78° C. solution of oxalyl chloride in CH₂Cl₂ (400 μL, 0.80 mmol, 2 M), rinsing with 1 mL CH₂Cl₂. The reaction was stirred at −78° C. for 30 min. and then a solution of 5 (297 mg, 0.49 mmol) in 1.2 mL CH₂Cl₂ was added dropwise by cannula, rinsing with 1.2 mL. Et₃N (400 μL, 2.9 mmol) was added and the reaction was allowed to warm to room temperature. After 5 h, 60 mL H₂O was added and the resulting mixture was extracted with CH₂Cl₂ (3×50 mL). The combined CH₂Cl₂ solution was washed with brine and then was dried (Na₂SO₄), filtered and evaporated. The residue was purified by flash chromatography on silica gel (0%→100% ethyl acetate/hexanes) to give the title compound (276 mg, 99%).

5-[3-((1S,2S)-2-{4-[1-(4-Methoxy-benzyloxy)-hexyl]-phenyl}-3-oxo-cyclopentyl)-propyl]-thiophene-2-carboxylic acid methyl ester (7). The [Ph₃PCuH]₆ procedure described in U.S. Provisional Patent Application No. 60/744,236, filed on Apr. 4, 2006 was used which gave the title compound (242 mg, 87%).

5-(3-{(1S,2S)-2-[4-(1-Hydroxy-hexyl)-phenyl]-3-oxo-cyclopentyl}-propyl)-thiophene-2-carboxylic acid methyl ester (8). The previously described DDQ procedure (U.S. patent application Ser. No. 11/009,298) was used. The individual diastereomers were obtained by HPLC separation at this stage and taken on to the corresponding free acid as shown in scheme 1 for the diastereomeric mixture. HPLC conditions: Chiralcel OD semiprep column (1 cm×25 cm), 10% isopropanol/hexanes, t$_R$=123, 138 min. (3 mg/injection).

5-(3-{(1S,2S)-2-[4-(1-Hydroxy-hexyl)-phenyl]-3-oxo-cyclopentyl}-propyl)-thiophene-2-carboxylic acid (9). The LiOH procedure described in U.S. patent application Ser. No. 11/009,298 was used with the exception that the reaction was run at 60° C. overnight.

Scheme 2

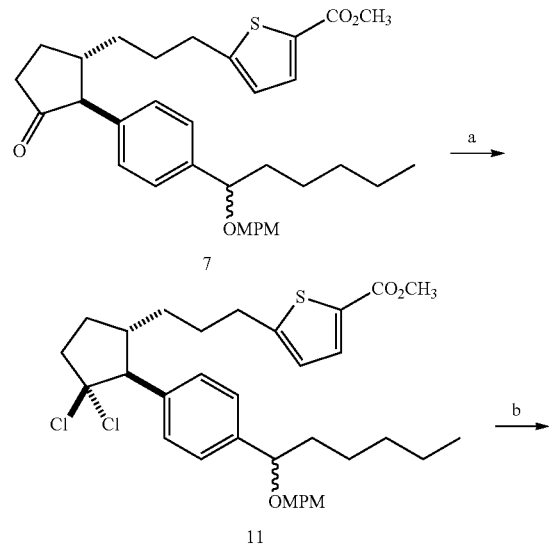

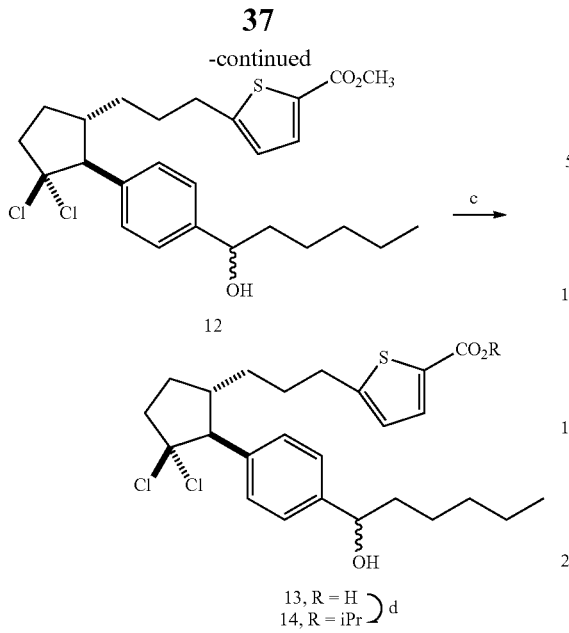

13, R = H  
14, R = iPr  } d

Conditions: (a) (TBSNH)₂, Sc(OTf)₃, CHCl₃; CuCl₂, Et₃N, CH₃OH;
(b) DDQ, ClCH₂CH₂Cl/H₂O; (c) aq. LiOH, THF 60° C.; (d) DBU, iPrI, acetone.

5-(3-{(1S,2S)-2-[4-(1-Hydroxy-hexyl)-phenyl]-3-oxo-cyclopentyl}-propyl)-thiophene-2-carboxylic acid isopropyl ester (10). The 2-iodopropane/DBU procedure described in U.S. patent application Ser. No. 11/009,298 was used.

5-[3-((1S,2S)-3,3-Dichloro-2-{4-[1-(4-methoxy-benzyloxy)-hexyl]-phenyl}-cyclopentyl)-propyl]-thiophene-2-carboxylic acid methyl ester (11). The procedure described in Furrow, M. E.; Myers, A. G. *J. Am. Chem. Soc.* 2004, 126, 5436 was followed: A solution of Sc(OTf)₃ (110 μL, 0.0011 mmol, 0.01 M/CH₃CN) was evaporated to dryness under vacuum. A solution of (TBSNH)₂ (143 mg, 0.55 mmol) in CHCl₃ (0.2 mL) was added by cannula, rinsing with 0.2 mL CHCl₃. The reaction was cooled to 0° C. and a solution of 7 (62 mg, 0.11 mmol) in 1 mL CHCl₃ was added by cannula, rinsing with 1 mL CHCl₃. The reaction was stirred overnight at room temperature, the CHCl₃ was removed under a N₂ stream, and the residue was heated at 55° C. under vacuum for 30 min.

The crude hydrazone was taken into 1 mL CHCl₃ and the resulting solution added dropwise to a mixture of CuCl₂ (107 mg, 0.80 mmol) and Et₃N (50 pt, 0.36 mmol) in methanol (1.2 mL), rinsing with 1 mL CHCl₃. The mixture was stirred in the dark for 1 h and then a 10% NH₄OH (aq)/saturated NH₄Cl solution (8 mL) was added. The resulting mixture was extracted with CH₂Cl₂ (3×30 mL) and the combined CH₂Cl₂ solution was dried (Na₂SO₄), filtered and evaporated. The residue was purified by flash chromatography on silica gel (0% 25% ethyl acetate/hexanes) to give the title compound (34 mg, 49%).

5-(3-{(1S,2S)-3,3-Dichloro-2-[4-(1-hydroxy-hexyl)-phenyl]-cyclopentyl}-propyl)-thiophene-2-carboxylic acid (12). The DDQ procedure described in U.S. patent application Ser. No. 11/009,298 was used which gave the title compound (13 mg, 72%).

5-(3-{(1S,2S)-3,3-Dichloro-2-[4-(1-hydroxy-hexyl)-phenyl]-cyclopentyl}-propyl)-thiophene-2-carboxylic acid (13). The LiOH procedure described in U.S. patent application Ser. No. 11/009,298 was used with the exception that the reaction was run at 60° C. overnight.

5-(3-{(1S,2S)-3,3-Dichloro-2-[4-(1-hydroxy-hexyl)-phenyl]-cyclopentyl}-propyl)-thiophene-2-carboxylic acid isopropyl ester (14). The 2-iodopropane/DBU procedure was used as described in U.S. Provisional Patent Application No. 60/742,779, filed on Dec. 6, 2005, which is expressly incorporated herein by reference.

Scheme 3

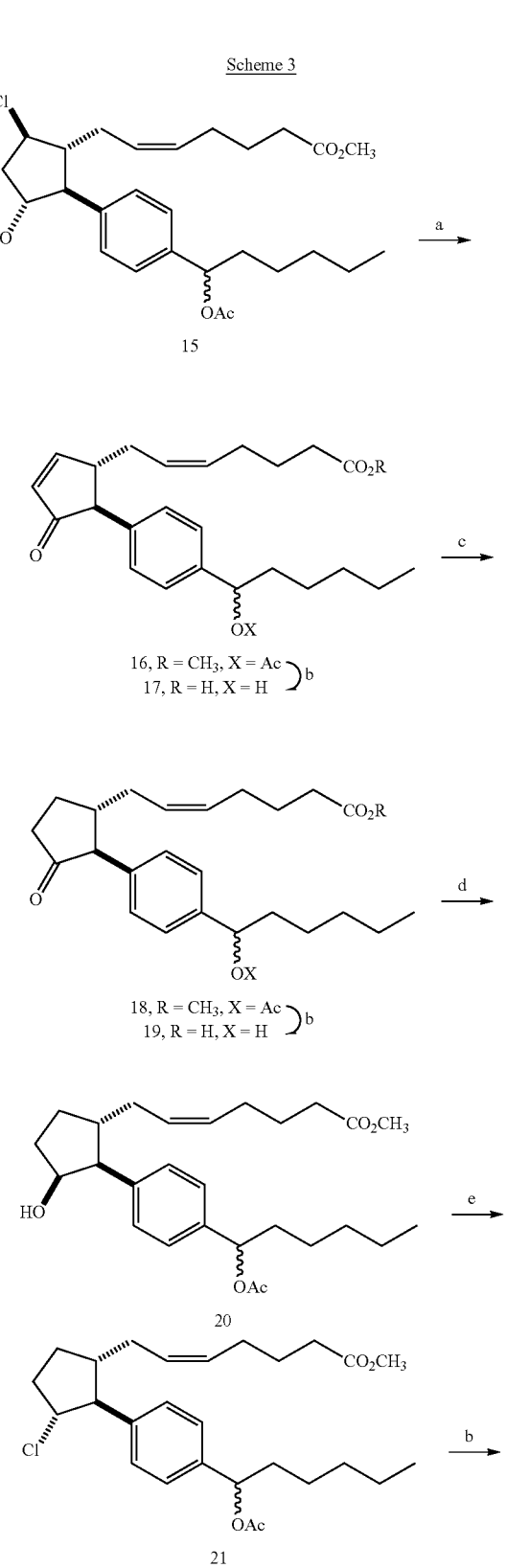

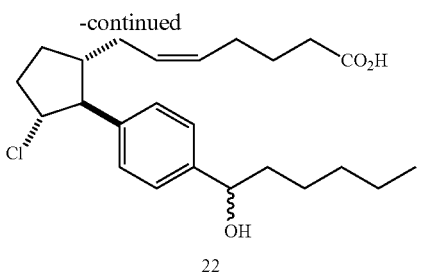

(a) Swern [O]; (b) 1M LiOH, THF; (c) [Ph₃PCuH]₆, toluene; (d) L-selectride; H₂O₂; (e) MsCl, Et₃N, ClCH₂Cl; (n-Bu)₄NCl, toluene 40° C.

(Z)-7-{(1R,2S,3R,5R)-2-[4-(1-Acetoxy-hexyl)-phenyl]-5-chloro-3-hydroxy-cyclopentyl}-hept-5-enoic acid methyl ester (15). Compound 15 was prepared as described in U.S. Provisional Patent Application No. 60/742,779.

(Z)-7-{(1S,5S)-5-[4-(1-Acetoxy-hexyl)-phenyl]-4-oxo-cyclopent-2-enyl}-hept-5-enoic acid methyl ester (16). The Swern oxidation procedure described for compound 6 was used.

(Z)-7-{(1S,5S)-5-[4-(1-Hydroxy-hexyl)-phenyl]-4-oxo-cyclopent-2-enyl}-hept-5-enoic acid (17). The previously described LiOH procedure was used (U.S. patent application Ser. No. 11/009,298).

(Z)-7-{(1R,2S)-2-[4-(1-Acetoxy-hexyl)-phenyl]-3-oxo-cyclopentyl}-hept-5-enoic acid methyl ester (18). The [Ph₃PCuH]₆ procedure described in U.S. Provisional Patent Application No. 60/744,236 was used which gave the title compound (127 mg, 61%).

(Z)-7-{(1R,2S)-2-[4-(1-Hydroxy-hexyl)-phenyl]-3-oxo-cyclopentyl}-hept-5-enoic acid (19). The previously described LiOH procedure was used (U.S. patent application Ser. No. 11/009,298).

(Z)-7-{(1R,2S,3S)-2-[4-(1-Acetoxy-hexyl)-phenyl]-3-hydroxy-cyclopentyl}hept-5-enoic acid methyl ester (20). The previously described L-Selectride procedure was used (U.S. patent application Ser. No. 11/009,298).

(Z)-7-{(1R,2S,3R)-2-[4-(1-Acetoxy-hexyl)-phenyl]-3-chloro-cyclopentyl}-hept-5-enoic acid methyl ester (21). The previously described mesylation/chlorination procedure was used (U.S. patent application Ser. No. 11/009, 298) which gave compound 21 (10 mg, 23%).

(Z)-7-{(1R,2S,3R)-3-Chloro-2-[4-(1-hydroxy-hexyl)-phenyl]-cyclopentyl}-hept-5-enoic acid (22). The previously described LiOH procedure was used (U.S. patent application Ser. No. 11/009,298).

Scheme 4

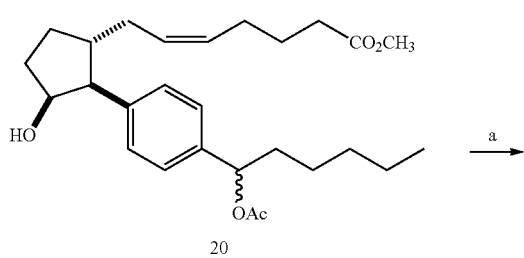

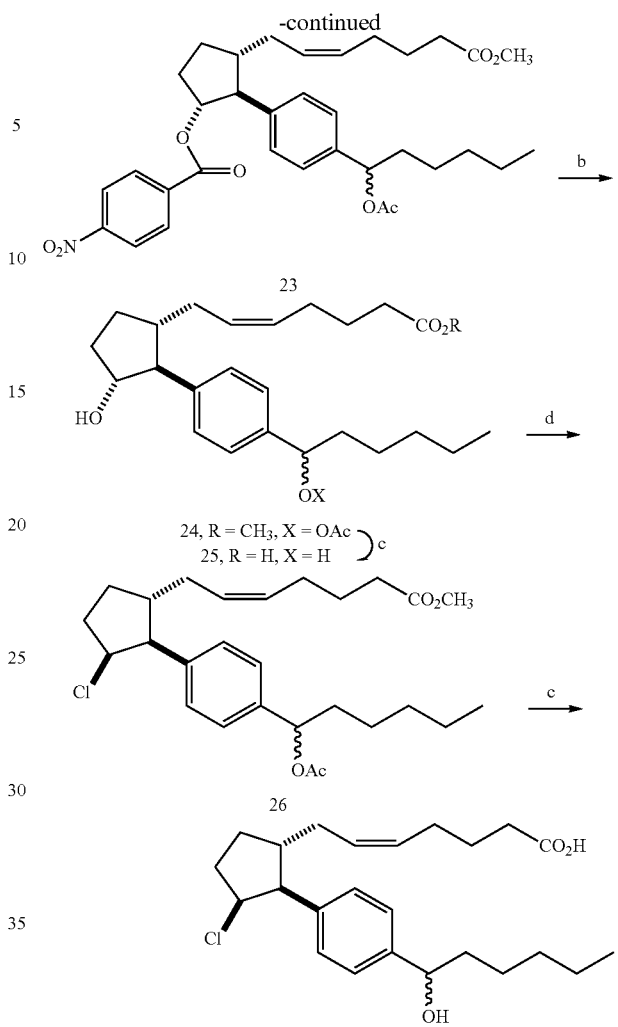

(a) 4-nitrobenzoic acid, PPh₃, diisopropyl azodicarboxylate, THF; (b) K₂CO₃, CH₃OH; (c) 1M LiOH, THF; (d) MsCl, Et₃N, ClCH₂CH₂Cl; (n-Bu)₄NCl, toluene 55° C.

4-Nitro-benzoic acid (1R,2S,3R)-2-[4-(1-acetoxy-hexyl)-phenyl]-3-((Z)-6-methoxycarbonyl-hex-2-enyl)-cyclopentyl ester (23). A solution of diisopropyl azodicarboxylate (85 μL, 0.44 mmol) in THF (1 mL) was added drop wise to an ice-cold mixture of 20 (77 mg, 0.17 mmol), 4-nitrobenzoic acid (62 mg, 0.37 mmol) and PPh₃ (109 mg, 0.42 mmol) in THF (2.5 ml), rinsing with 1 mL THF. The reaction was allowed to warm to room temperature, was stirred overnight and then the volatiles were removed. The residue was purified by flash chromatography on silica gel (20% ethyl acetate/hexanes) to give the title compound (53 mg, 53%).

(Z)-7-{(1R,2S,3R)-2-[4-(1-Acetoxy-hexyl)-phenyl]-3-hydroxy-cyclopentyl}-hept-5-enoic acid methyl ester (24). A mixture of 23 (53 mg, 0.09 mmol) and K₂CO₃ (7 mg, 0.05 mmol) in CH₃OH (2.6 mL) was stirred for 1 h. Saturated NH₄Cl solution (20 mL) was added and the resulting mixture was extracted with ethyl acetate (3×20 mL). The combined ethyl acetate solution was dried (Na₂SO₄), filtered and evaporated. The residue was purified by flash chromatography on silica gel (40% ethyl acetate/hexanes) to give the title compound (27 mg, 67%) along with the deacetylated side product (9 mg, 26%).

(Z)-7-{(1R,2S,3R)-3-Hydroxy-2-[4-(1-hydroxy-hexyl)-phenyl]-cyclopentyl}-hept-5-enoic acid (25). The previously described LiOH procedure was used (U.S. patent application Ser. No. 11/009,298).

(Z)-7-{(1R,2S,3S)-2-[4-(1-Acetoxy-hexyl)-phenyl]-3-chloro-cyclopentyl}-hept-5-enoic acid methyl ester (26). The previously described mesylation/chlorination procedure was followed (U.S. patent application Ser. No. 11/009,298), with the exception that the chloride displacement step was done at 55° C. instead of the usual 40° C. which gave the title compound (10 mg, 37%).

(Z)-7-{(1R,2S,3S)-3-Chloro-2-[4-(1-hydroxy-hexyl)-phenyl]-cyclopentyl}-hept-5-enoic acid (27). The previously described LiOH procedure was used (U.S. patent application Ser. No. 11/009,298).

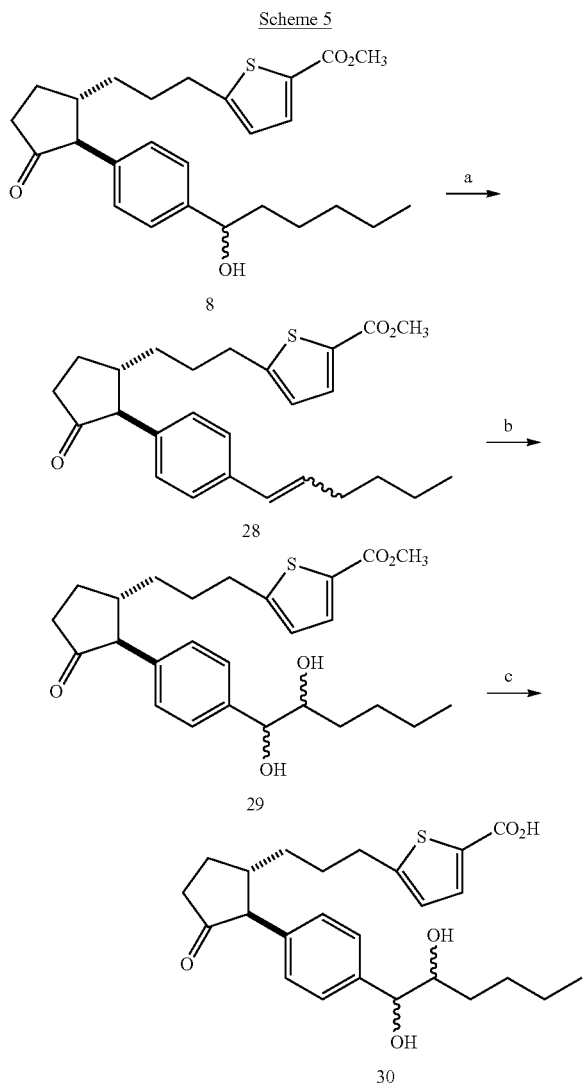

Conditions: (a) Burgess reagent, $C_6H_6$ 50° C.; (b) $OsO_4$, NMO, acetone; (c) Rabbit Liver Esterase.

(Z)-7-[(1R,2S)-2-(4-Hex-1-enyl-phenyl)-3-oxo-cyclopentyl]-hept-5-enoic acid methyl ester (28). A solution of alcohol 8 (37 mg, 0.08 mmol) in benzene (0.5 mL) was added to a solution of the Burgess reagent [(methoxycarbonylsulfamoyl)triethylammonium hydroxide, inner salt, 81 mg, 0.34 mmol] in benzene (0.5 mL) by cannula, rinsing with 0.5 mL benzene. The reaction was heated at 50° C. for 3 h and was then quenched by addition of saturated $NH_4Cl$ solution. The mixture was extracted with dichloromethane (3×25 mL) and the combined organic solution was dried ($Na_2SO_4$), filtered and evaporated. Purification by flash chromatography on silica gel (0→100% ethyl acetate/hexane) gave the title compound (12 mg, 34%).

(Z)-7-{(1R,2S)-2-[4-(1,2-Dihydroxy-hexyl)-phenyl]-3-oxo-cyclopentyl}-hept-5-enoic acid methyl ester (29). $OsO_4$ (90 μL, 0.015 mmol, 4 wt. %/$H_2O$) was added to an ice cold mixture of alkene 28 (12 mg, 0.029 mmol) and NMO (13 mg, 0.11 mmol) in acetone (0.6 mL). The reaction was allowed to warm to room temperature and after 1 h, 5 mL 5% $NaHCO_3$ solution was added. The mixture was extracted with ethyl acetate (3×) and the combined ethyl acetate solution was washed with brine and then was dried ($Na_2SO_4$), filtered and evaporated. Purification by flash chromatography on silica gel provided the title compound (9 mg, 67%).

(Z)-7-{(1R,2S)-2-[4-(1,2-Dihydroxy-hexyl)-phenyl]-3-oxo-cyclopentyl}-hept-5-enoic acid (30).

4-(2-{(1S,2S)-2-[4-(1-Hydroxy-hexyl)-phenyl]-3-oxo-cyclopentyl}-ethyl)-benzoic acid. The title compound was prepared in an analogous sequence to compound 9.

5-(3-{(1S,5S)-5-[4-(1-Hydroxy-hexyl)-phenyl]-4-oxo-cyclopent-2-enyl}-propyl)-thiophene-2-carboxylic acid. The title compound was prepared in an analogous sequence to compound 9.

Compounds such as those depicted in the structure on the right below may be prepared as described in Krishnamurti as depicted below. Use of protecting groups for additional carbonyl groups which can be part of $M^4$ may be necessary. Standard protection and deprotection is known in the art to carry this out. The fluoroalkylation may also be carried out an earlier point in the synthetic procedure. Such decisions are well within the knowledge of one of ordinary skill in the art.

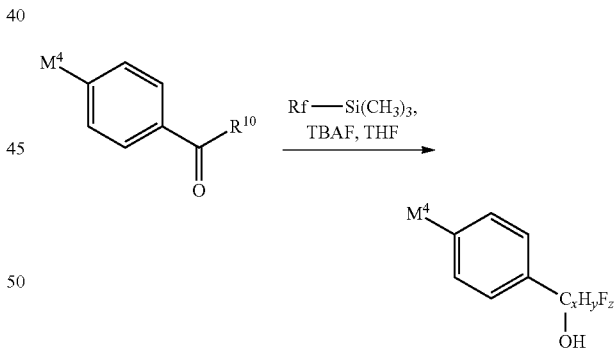

$R^{10}$: H, hydrocarbyl Rf: fluorocarbon

Krishnamurti et. al. *J. Org. Chem*, 1991, 56, 984-989.

Binding Data

Ki

Competition binding experiments were performed in a medium containing Hank's balanced salt solution, Hepes 20 mM, pH 7.3, membranes (~60 μg protein) or 2×10⁵ cells from HEK 293 cells stably expressing human EP2 receptors, [³H] PGE2 (10 nM) and various concentrations of test compounds in a total volume of 300 μl. Reaction mixtures were incubated at 23° C. for 60 min, and were filtered over Whatman GF/B filters under vacuum. Filters were washed three times with 5 ml ice-cold buffer containing 50 mM Tris/HCl (pH 7.3).

Non-specific binding was estimated in the presence of excess unlabeled PGE2 (10 μM). Binding data fitted to the binding model for a single class of binding sites, using nonlinear regression analysis. $IC_{50}$ values thus obtained were converted to Ki using the equation of $Ki=(IC_{50}/(1+[L]/KD)$ where [L] represents PGE2 concentration (10 nM) and KD the dissociation constant for [$^3$H]PGE2 at human EP2 receptors (40 nM).

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-]17-phenyl PGF2, (5 nM) were performed in a 100 μl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour.

[$^3$H-] PGE2 (specific activity 180 Ci mmol) was used as the radioligand for EP receptors. [$^3$H] 17-phenyl $PGF_2$, was employed for FP receptor binding studies. Binding studies employing $EP_1$, $EP_2$, $EP_4$ and FP receptors were performed in duplicate in at least three separate experiments. A 200 μl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [$^3$H]-$PGE_2$, or 5 nM [$^3$H] 17-phenyl $PGF_{2\alpha}$ and non-specific binding determined with $10^{-5}$M of unlabeled $PGE_2$, or 17-phenyl $PGF_{2\alpha}$, according to receptor subtype studied.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; $hEP_1$; $hEP_2$/Gqs5; $hEP_{3A}$/Gqi5; $hEP_4$/Gqs5; hFP; hIP; hTP), were cultured in 100 mm culture dishes in high-glucose DMEM medium containing 10% fetal bovine serum, 2 mM I-glutamine, 250 g/ml geneticin (G418) and 200 μg/ml hygromycin B as selection markers, and 100 units/ml penicillin G, 100 g/ml streptomycin and 0.25 μg/ml amphotericin B.

(b) Calcium Signal Studies on the FLIPR™

Cells were seeded at a density of $5 \times 10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 μM, plates were washed four times with HBSS-HEPES buffer to remove excess dye leaving 100 μl in each well. Plates were re-equilibrated to 37° C. for a few minutes.

Cells were excited with an Argon laser at 488 nm, and emission was measured through a 510-570 nm bandwidth emission filter (FLIPR™, Molecular Devices, Sunnyvale, Calif.). Drug solution was added in a 50 l volume to each well to give the desired final concentration. The peak increase in fluorescence intensity was recorded for each well. On each plate, four wells each served as negative (HBSS-HEPES buffer) and positive controls (standard agonists: BW245C (hDP); $PGE_2$ ($hEP_1$; $hEP_2$/Gqs5; $hEP_{3A}$/Gqi5; $hEP_4$/Gqs5); $PGF_{2\alpha}$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$ M. The duplicate values were averaged. In either, HTS or CoRe format each compound was tested on at least 3 separate plates using cells from different passages to give an $n \geq 3$.

The results of the binding and activity studies, presented in Tables 1 demonstrate that the compounds disclosed herein are selective prostaglandin $EP_2$ agonists, and are thus useful for the treatment of glaucoma and ocular hypertension.

TABLE 1

| Entry | STRUCTURE[a] | BINDING-KI (nm) | | $Ca^{2+}$ Signal-EC50 (nm)[b] | | | | | | | |
|---|---|---|---|---|---|---|---|---|---|---|---|
| | | EP2 | EP4 | FP | EP1 | EP2 | EP3 | EP4 | TP | IP | DP |
| 1 | *(structure: low retention time diastereomer)* | 43 | | not active | not active | 62 (5) | 8775 | >10,000 | not active | not active | not active | low retention time diastereomer

TABLE 1-continued

| Entry | STRUCTURE[a] | BINDING-KI (nm) | | Ca²⁺ Signal-EC50 (nm)[b] | | | | | | | |
|---|---|---|---|---|---|---|---|---|---|---|---|
| | | EP2 | EP4 | FP | EP1 | EP2 | EP3 | EP4 | TP | IP | DP |
| 2 | high retention time diastereomer | 70 | | not active | not active | 25 (9) | not active | not active | not active | not active | 9057 |
| 3 | | 89 | | not active | not active | 1623 (3) | not active | not active | not active | not active | not active |
| 4 | | >10,000 | 4328 | | | | | not active | | | |
| 5 | | 1051 | 4207 | not active | not active | 381 (34) | 4421 | not active | not active | not active | not active |

TABLE 1-continued

| Entry | STRUCTURE[a] | BINDING-KI (nm) | | Ca²⁺ Signal-EC50 (nm)[b] | | | | | | | |
|---|---|---|---|---|---|---|---|---|---|---|---|
| | | EP2 | EP4 | FP | EP1 | EP2 | EP3 | EP4 | TP | IP | DP |
| 6 | | 401 | 1030 | not active | not active | 731 (94) | 182 | not active | not active | not active | not active |
| 7 | | 2309 | | not active | not active | 2506 (73) | 3478 | >10,000 | not active | not active | not active |
| 8 | | 2994 | 1520 | not active | not active | 7811 (4984) | 4343 | 4899 | not active | not active | not active |
| 9 | | 13 | | not active | not active | 2120 (2) | not active | not active | not active | not active | not active |

TABLE 1-continued

| Entry | STRUCTURE[a] | BINDING-KI (nm) | | Ca$^{2+}$ Signal-EC50 (nm)[b] | | | | | | | |
|---|---|---|---|---|---|---|---|---|---|---|---|
| | | EP2 | EP4 | FP | EP1 | EP2 | EP3 | EP4 | TP | IP | DP |
| 10 | [structure] | | | | | not active | | not active | | | |
| 11 | [structure] | 173 | 1938 | not active | not active | 208 (9) | 4552 | >10K | not active | not active | not active |

[a]All compounds are mixtures of diastereomers except where indicated
[b]Data in parenthesis refer to cAMP measurement (see experimental for details)

In Vitro Testing

U.S. patent application Ser. No. 11/553,143, filed on Oct. 26, 2006, incorporated by reference herein, describes the methods used to obtain the in vitro data in the table below.

Chemistry, New York: McGraw-Hill Book Company 1987, p. 63) states "a wedge indicates a bond coming from the plane of the paper toward the viewer" and the hatched wedge, indicated as a "dashed line", "represents a bond receding from the viewer."

TABLE 2

| ENTRY | STRUCTURE | Conc. (g/100 mL) | DOG Max. ΔIOP (%) | DOG Max. hyperemia | MONKEY Max. ΔIOP (%) | RABBIT Max. hyperemia |
|---|---|---|---|---|---|---|
| 1 | [structure] (mixture of diastereomers) | 0.1% | −37 | 1.6 | | |
| 2 | [structure] | 0.1% | −6 | 0.4 | −21 | |

A person of ordinary skill in the art understands the meaning of the stereochemistry associated with the hatched wedge/solid wedge structural features. For example, an introductory organic chemistry textbook (Francis A. Carey, Organic Treatment of inflammatory bowel disease may be accomplished by the administration of the compounds described herein to the suffering mammal. Inflammatory bowel disease describes a variety of diseases characterized by inflammation of the bowels including, but not limited to, ulcerative colitis and Crohn's disease. Treatment may be accomplished by oral administration, by suppository, or parenteral administration, or some other suitable method.

While not intending to limit the scope of the invention in any way, delivery of the compounds disclosed herein to the colon via oral dosage forms may be accomplished by any of a number of methods known in the art. For example, reviews by Chourasia and Jain in J Pharm Pharmaceut Sci 6 (1): 33-66, 2003 and Shareef et. al (AAPS PharmSci 2003; 5 (2) Article 17) describe a number of useful methods. While not intending to limit the scope of the invention in any way these methods include 1) administration of a prodrug, including an azo or a carbohydrate based prodrug; 2) coating the drug with, or encapsulating or impregnating the drug into a polymer designed for delivery to the colon, 3) time released delivery of the drug, 4) use of a bioadhesive system; and the like.

While not intending to be bound in any way by theory, it is believed that intestinal microflora are capable of reductive cleavage of an azo bond leaving the two nitrogen atoms as amine functional groups. While not intending to limit the scope of the invention in any way, the azo prodrug approach has been used to deliver to 5-aminosalicylic acid to the colons of humans in clinical trials for the treatment of inflammatory bowel disease. It is also believed that bacteria of the lower GI also have enzymes which can digest glycosides, glucuronides, cyclodextrins, dextrans, and other carbohydrates, and ester prodrugs formed from these carbohydrates have been shown to deliver the parent active drugs selectively to the colon. For example, in vivo and in vitro studies on rats and guinea pigs with prodrugs of dexamethasone, prednisolone, hydrocortisone, and fludrocortisone, suggest that glycoside conjugates may be useful for the delivery of steroids to the human colon. Other in vivo studies have suggested that glucouronide, cyclodextrin, and dextran prodrugs of steroids or non-steroidal anti-inflammatory drugs are useful for delivery of these drugs to the lower GI tract. An amide of salicylic acid and glutamic acid has been shown to be useful for the delivery of salicylic acid to the colon of rabbit and dog.

While not intending to limit the scope of the invention in any way, carbohydrate polymers such as amylase, arabinogalactan, chitosan, chondroiton sulfate, dextran, guar gum, pectin, xylin, and the like, or azo-group containing polymers can be used to coat a drug compound, or a drug may be impregnated or encapsulated in the polymer. It is believed that after oral administration, the polymers remain stable in the upper GI tract, but are digested by the microflora of the lower GI thus releasing the drug for treatment.

Polymers which are sensitive to pH may also be used since the colon has a higher pH than the upper GI tract. Such polymers are commercially available. For example, Rohm Pharmaceuticals, Darmstadt, Germany, commercially provides pH dependent methacrylate based polymers and copolymers which have varying solubilities over different pH ranges based upon the number of free carboxylate groups in the polymer under the tradename Eudragit®. Several Eudragit® dosage forms are currently used to deliver salsalazine for the treatment of ulcerative colitis and Crohn's disease. Time release systems, bioadhesive systems, and other delivery systems have also been studied.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:

1. A method of growing hair or improving the appearance of hair, comprising administering to a mammal in need thereof a compound of structure:

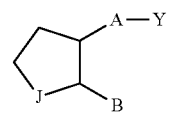

or a pharmaceutically acceptable salt thereof, or an ester prodrug thereof;

wherein Y is selected from $CO_2R^2$, $CON(R^2)2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$, wherein $R^2$ is independently H, $C_1$-$C_{12}$ alkyl, unsubstituted phenyl, or unsubstituted biphenyl;

A is —$(CH_2)_6$—, cis —$CH_2CH$=$CH$—$(CH_2)_3$—, or —$CH_2C$≡$C$—$(CH_2)_3$—, wherein 1 or 2 carbon atoms may be replaced by S or O; or A is —$(CH_2)_m$—Ar—$(CH_2)_o$ wherein Ar is interarylene or heterointerarylene, the sum of m and o is 1, 2, 3, or 4, and wherein one $CH_2$ may be replaced by S or O;

J is C=O, CHOH, CHF, CHCl, CHBr, $CF_2$, $CCl_2$, $CBr_2$, or CHCN; and

B is substituted aryl or substituted heteroaryl.

2. The method of claim 1 wherein the compound is selected from:

5-(3-{(1S,2S)-2-[4-(1-Hydroxy-hexyl) -phenyl]-3-oxo-cyclopentyl}-propyl)-thiophene-2-carboxylic acid;

5-(3-{(1S,2S)-2-[4-(1-Hydroxy-hexyl)-phenyl]-3-oxo-cyclopentyl}-propyl)-thiophene-2-carboxylic acid methyl ester;

5-(3-{(1S,2S)-2-[4-(1-Hydroxy-hexyl)-phenyl]-3-oxo-cyclopentyl}-propyl)-thiophene-2-carboxylic acid isopropyl ester;

5-(3-{(1S,2S)-2-[4-((R)-1-Hydroxy-hexyl) -phenyl]-3-oxo-cyclopentyl}-propyl)-thiophene-2-carboxylic acid;

5-(3-{(1S,2S)-2-[4-((R)-1-Hydroxy-hexyl) -phenyl]-3-oxo-cyclopentyl}-propyl)-thiophene-2-carboxylic acid methyl ester;

5-(3-{(1S,2S)-2-[4-((R)-1-Hydroxy-hexyl) -phenyl]-3-oxo-cyclopentyl}-propyl)-thiophene-2-carboxylic acid isopropyl ester;

5-(3-{(1S,2S)-2-[4-((S)-1-Hydroxy -hexylyphenyl]-3-oxo-cyclopentyl}-propyl)-thiophene-2-carboxylic acid;

5-(3-{(1S,2S)-2-[4-((S)-1-Hydroxy -hexylyphenyl]-3-oxo-cyclopentyl}-propyl)-thiophene-2-carboxylic acid methyl ester;

5-(3-{(1S,2S)-2-[4-((S)-1-Hydroxy -hexylyphenyl]-3-oxo-cyclopentyl}-propyl)-thiophene-2-carboxylic acid isopropyl ester;

5-(3-{(1S,2S)-3,3-Dichloro-2-[4-(1-hydroxy-hexyl)-phenyl]-cyclopentyl}-propyl)-thiophene-2-carboxylic acid;

5-(3-{(1S,2S)-3,3-Dichloro-2-[4-(1-hydroxy-hexyl)-phenyl]-cyclopentyl}-propyl)-thiophene-2-carboxylic acid methyl ester;
(Z)-7-{(1S,5S)-5-[4-(1-Hydroxy-hexyl)-phenyl]-4-oxo-cyclopent-2-enyl}-hept-5-enoic acid;
(Z)-7-{(1S,5S)-5-[4-(1-Hydroxy-hexyl)-phenyl]-4-oxo-cyclopent-2-enyl}-hept-5-enoic acid isopropyl ester;
(Z)-7-{(1R,2S)-2[4-(1-Hydroxy-hexyl)-phenyl]-3-oxo-cyclopentyl}-hept-5-enoic acid;
(Z)-7-{(1R,2S)-2-[4-(1-Hydroxy-hexyl)-phenyl]-3-oxo-cyclopentyl}-hept-5-enoic acid isopropyl ester;
(Z)-7-{(1R,2S,3R)-3-Chloro-2-[4-(1-hydroxy-hexyl)-phenyl]-cyclopentyl}-hept-5-enoic acid;
(Z)-7-{(1R,2S,3R)-3-Chloro-2-[4-(1-hydroxy-hexyl)-phenyl]-cyclopentyl}-hept-5-enoic acid isopropyl ester;
(Z)-7-{(1R,2S,3R)-3-Hydroxy-2-[4-(1-hydroxy-hexyl)-phenyl]-cyclopentyl}-hept-5-enoic acid;
(Z)-7-{(1R,2S,3R)-3-Hydroxy-2-[4-(1-hydroxy-hexyl)-phenyl]-cyclopentyl}-hept-5-enoic acid isopropyl ester;
(Z)-7-{(1R,2S,3S)-3-Chloro-2[4-(1-hydroxy-hexyl)-phenyl]-cyclopentyl}-hept-5-enoic acid; or
(Z)-7-{(1R,2S,3S)-3-Chloro-2[4-(1-hydroxy-hexyl)-phenyl]-cyclopentyl}-hept-5-enoic acid isopropyl ester.

3. The method of claim 1 wherein the hair is eyelash hair.
4. The method of claim 1 wherein the hair is eyebrow hair.
5. The method of claim 1 wherein the mammal is a human being.
6. The method of claim 1 wherein J is C=O.
7. The method of claim 6 wherein the hair is eyelash hair.
8. The method of claim 1 wherein J is $CCl_2$.
9. The method of claim 8 wherein the hair is eyelash hair.
10. The method claim 1 wherein J is CHCl.
11. The method of claim 10 wherein the hair is eyelash hair.
12. The method of claim 1 wherein J is CHOH.
13. The method of claim 12 wherein the hair is eyelash hair.
14. The method of claim 1, wherein B is substituted phenyl.
15. The method of claim 14 wherein the hair is eyelash hair.
16. The method of claim 1, wherein B is 4-(1-hydroxy-hexyl)phenyl.
17. The method of claim 16 wherein the hair is eyelash hair.
18. The method of claim 1, wherein A is 5-(3-propyl)thiophen-2-yl.
19. The method of claim 18 wherein the hair is eyelash hair.
20. The method of claim 2 wherein the hair is eyelash hair.

* * * * *